United States Patent
Karasawa et al.

(10) Patent No.: US 8,237,782 B2
(45) Date of Patent: Aug. 7, 2012

(54) MEDICAL INSTRUMENT WITH MECHANISM FOR REMOVING CONTAMINANT ON OBSERVATION WINDOW

(75) Inventors: Hitoshi Karasawa, Hachioji (JP); Sho Nakajima, Hachioji (JP); Daisuke Asada, Hachioji (JP); Nobuyoshi Yazawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 142 days.

(21) Appl. No.: 12/719,329

(22) Filed: Mar. 8, 2010

(65) Prior Publication Data

US 2010/0225753 A1    Sep. 9, 2010

Related U.S. Application Data

(63) Continuation of application No. PCT/JP2009/066296, filed on Sep. 17, 2009.

(30) Foreign Application Priority Data

Oct. 16, 2008 (JP) ................................. 2008-267879

(51) Int. Cl.
*A62B 1/04* (2006.01)
*A61B 1/04* (2006.01)

(52) U.S. Cl. ........................................ 348/65; 600/122

(58) Field of Classification Search ............. 348/65; 600/122

See application file for complete search history.

(56) References Cited

U.S. PATENT DOCUMENTS

2007/0299301 A1    12/2007   Uchiyama et al.
2010/0174144 A1*   7/2010    Hsu et al. ............. 600/122

FOREIGN PATENT DOCUMENTS

| JP | 08-029699 | 2/1996 |
|---|---|---|
| JP | 2001-170084 | 6/2001 |
| JP | 2005-040184 | 2/2005 |
| JP | 2006-055275 | 3/2006 |
| JP | 2006-149668 | 6/2006 |
| JP | 2007-130084 | 5/2007 |
| JP | 2007-159641 | 6/2007 |
| JP | 2007-194931 | 8/2007 |
| WO | WO 2006/057443 A1 | 6/2006 |

OTHER PUBLICATIONS

International Search Report dated Oct. 27, 2009.

* cited by examiner

*Primary Examiner* — Jay Patel
*Assistant Examiner* — Richard Torrente
(74) *Attorney, Agent, or Firm* — Scully, Scott, Murphy & Presser, P.C.

(57) ABSTRACT

A medical instrument used by being introduced into a body and fixed thereto, includes a camera body provided with a fixing section to be fixed to a body wall in the body, an image pickup section incorporated in the camera body that picks up an image of an object to be examined in the body from an observation window formed in the camera body, a contamination removing section provided by being fixed to the camera body, a transparent cover member, an outer surface of which is in contact with the contamination removing section, movably disposed on the observation window and a drive section incorporated in the camera body that drives the cover member to make a sliding contact with the contamination removing section, and can thereby easily and reliably remove deposits stuck to the observation window and obtain a clear observation image even when deposits are being removed.

6 Claims, 25 Drawing Sheets

US 8,237,782 B2

MEDICAL INSTRUMENT WITH MECHANISM FOR REMOVING CONTAMINANT ON OBSERVATION WINDOW

CROSS REFERENCE TO RELATED APPLICATION

This application is a continuation application of PCT/JP2009/066296 filed on Sep. 17, 2009 and claims benefit of Japanese Application No. 2008-267879 filed in Japan on Oct. 16, 2008; the entire contents of which are incorporated herein by this reference.

BACKGROUND OF THE INVENTION

1. Field of the Invention

The present invention relates to a medical instrument provided with image pickup means which is left indwelling and fixed to the inside of the abdominal wall of a patient.

2. Description of the Related Art

As is well known, endoscope apparatuses, which are medical instruments, are provided with an image pickup apparatus, which is image pickup means, designed to be introduced into a body cavity of a patient and perform various types of inspections and treatments of affected areas in the body based on observed images taken by the image pickup apparatus. Examples of such endoscopes include those introduced into digestive organs such as esophagus, stomach, large intestine and duodenum, which are tube cavities and tubes in the body, from the oral cavity or anus and those introduced into the abdominal cavity from the vicinity of the umbilical region by puncturing through the body wall.

Endoscope apparatuses for medical treatment are used in such an environment that contamination such as mucous membranes, bodily waste or blood in the body is stuck to the observation window of the image pickup apparatus or vapor is stuck to the observation window of the image pickup apparatus in a humid environment inside the body to cause fogging of the observation window, and these deposits may thereby impair visibility, preventing clear taken images from being acquired. Thus, conventionally, various proposals to remove deposits stuck to the observation window of image pickup apparatuses have been presented.

For example, Japanese Patent Application Laid-Open Publication No. 8-29699 discloses an image scope provided with a wiper that wipes contamination off the outer surface of an objective lens. Furthermore, for example, Japanese Patent Application Laid-Open Publication No. 2001-170084 discloses a tooth brushing apparatus provided with a video scope including a nozzle for removing deposits stuck to the optical window of the video scope on which image taking light impinges by a jet of water.

Furthermore, for example, Japanese Patent Application Laid-Open Publication No. 2006-55275 discloses an endoscope apparatus including an image capturing window provided with a cover glass, on the outer surface of which a hydrophilic-processed coating layer is formed, wherein contamination is removed by selectively applying ultrasound vibration to the cover glass. Japanese Patent Application Laid-Open Publication No. 2006-55275 discloses a configuration of the endoscope apparatus provided with a wiper in sliding contact with the cover glass that removes deposits.

Though not classified as a medical instrument, Japanese Patent Application Laid-Open Publication No. 2007-194931 discloses an image pickup apparatus provided with a cleaning section that deforms by receiving a predetermined stimulus applied, comes into contact with or goes away from an optical element or image pickup device due to the deformation, and thereby causes the contacting section thereof to clean deposits stuck to the lens.

As described above, the related arts adopt a configuration of removing deposits stuck to the observation window of the image pickup apparatus by a jet of water or a wiper.

SUMMARY OF THE INVENTION

A medical instrument according to the present invention is a medical instrument used by being introduced into a body and fixed thereto, including a camera body provided with a fixing section to be fixed to a body wall in the body, an image pickup section incorporated in the camera body that picks up an image of an object to be examined in the body from an observation window formed in the camera body, a contamination removing section provided by being fixed to the camera body, a transparent cover member, an outer surface of which is in contact with the contamination removing section, movably disposed on the observation window and a drive section incorporated in the camera body that drives the cover member to make a sliding contact with the contamination removing section.

DETAILED DESCRIPTION OF THE PREFERRED EMBODIMENTS

Hereinafter, embodiments of the present invention will be described based on the accompanying drawings. A medical instrument provided with image pickup means used, for example, for a laparoscopic surgical operation will be illustrated in the following descriptions.

First Embodiment

Figure 1:
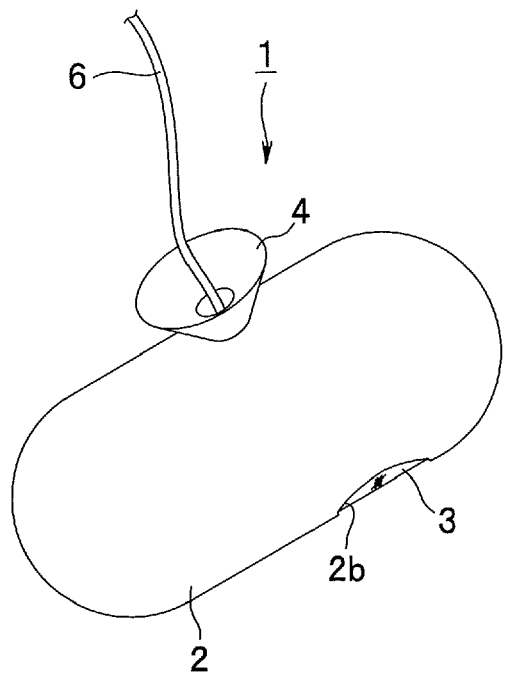
FIG. 1 is a perspective view illustrating a configuration of a camera set up in the abdominal cavity according to a first embodiment of the present invention.
Figure 2:
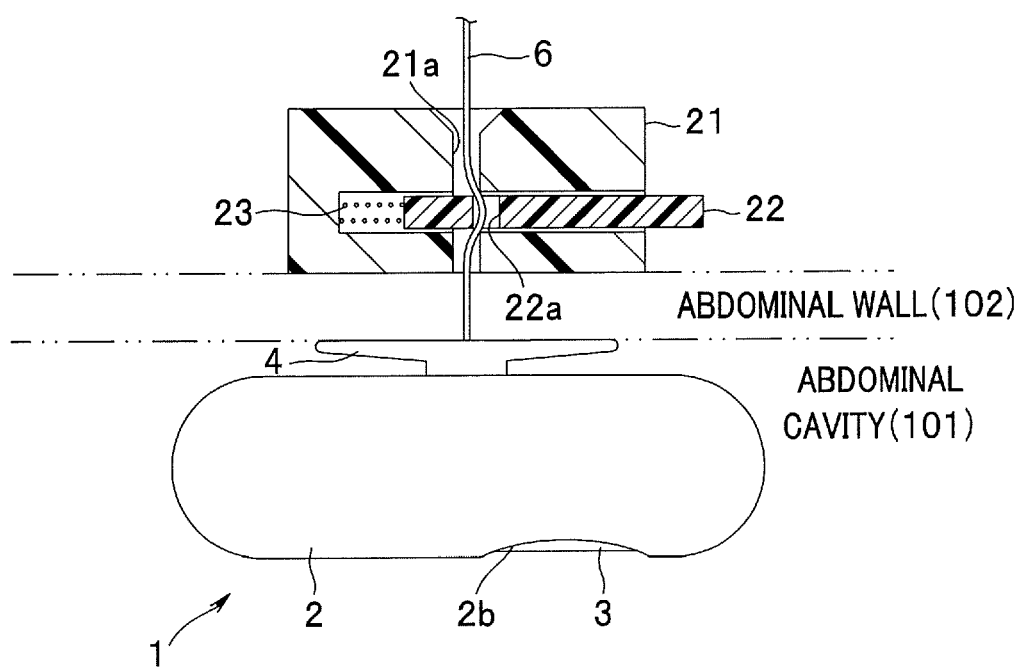
FIG. 2 is a partial cross-sectional view of the camera set up in the abdominal cavity according to the first embodiment of the present invention illustrating how the camera is set up in the abdominal cavity.
Figure 3:
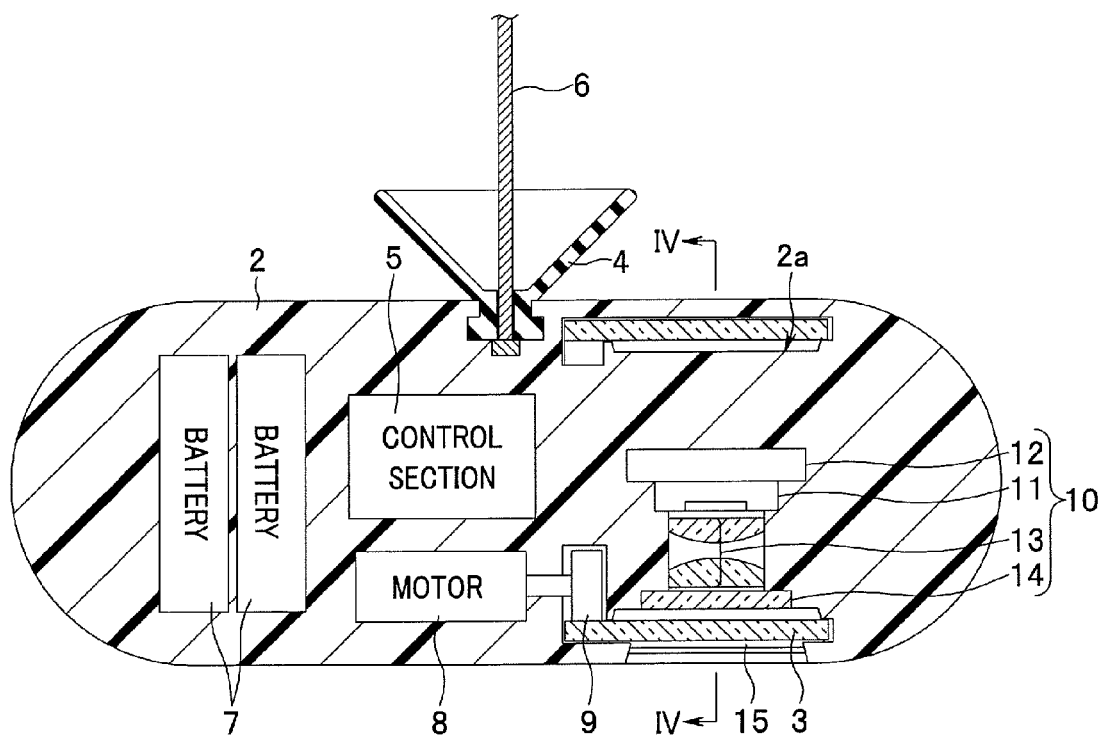
FIG. 3 is a cross-sectional view illustrating the configuration of the camera set up in the abdominal cavity according to the first embodiment of the present invention.
Figure 4:
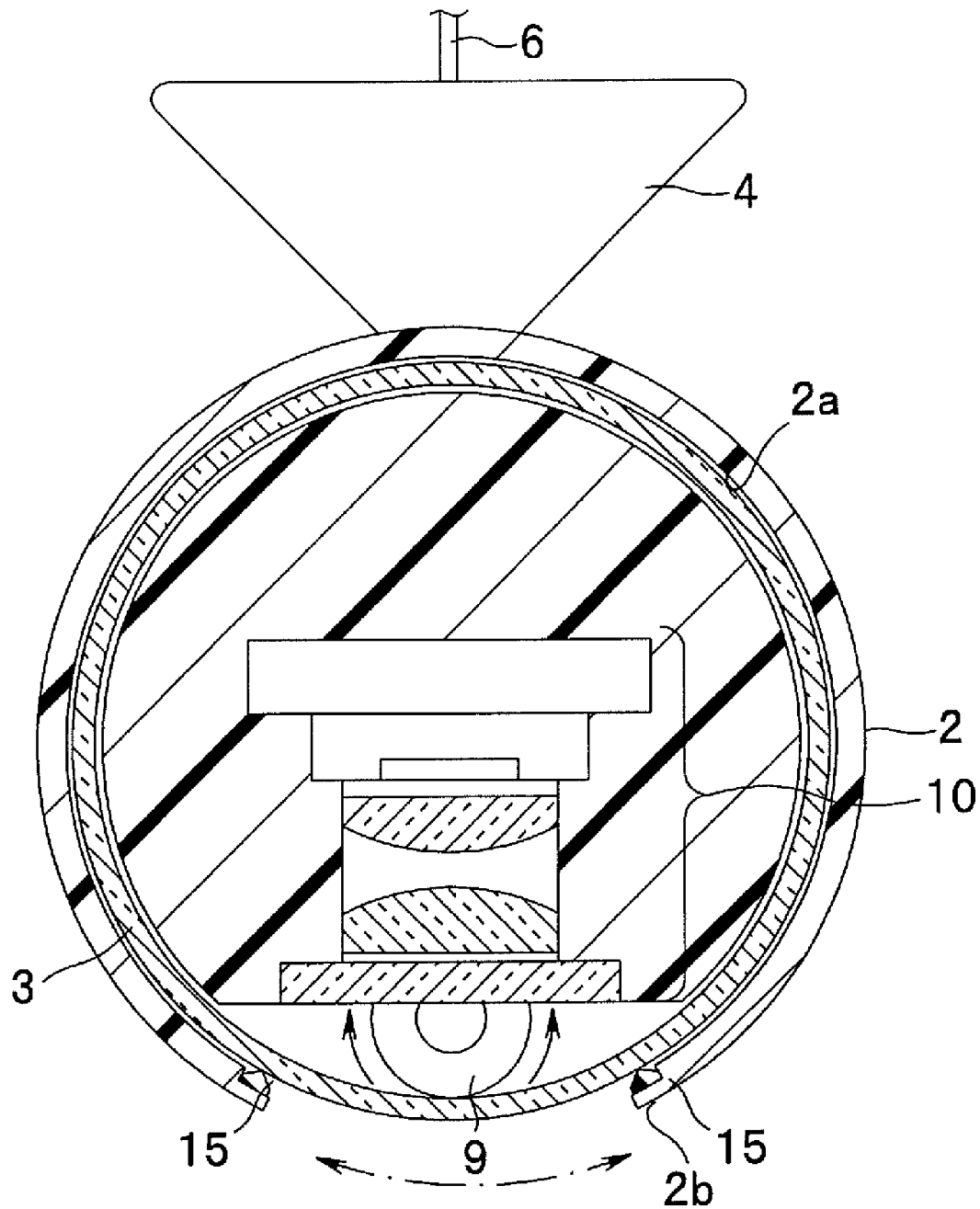
FIG. 4 is cross-sectional view along a line IV-IV in FIG. 3 illustrating the configuration of the camera set up in the abdominal cavity according to the first embodiment of the present invention.

First, the camera set up in the abdominal cavity, which is a medical instrument, according to the present invention used for a laparoscopic surgical operation will be described below. FIG. 1 to FIG. 4 are related to a first embodiment of the present invention, FIG. 1 is a perspective view illustrating a configuration of the camera set up in the abdominal cavity, FIG. 2 is a partial cross-sectional view illustrating how the camera set up in the abdominal cavity is set up in the abdominal cavity, FIG. 3 is a cross-sectional view illustrating the configuration of the camera set up in the abdominal cavity and FIG. 4 is a cross-sectional view along a line IV-IV in FIG. 3 illustrating the configuration of the camera set up in the abdominal cavity.

As shown in FIG. 1 to FIG. 4, the camera set up in the abdominal cavity (hereinafter simply referred to as "camera") 1, which is a medical instrument, according to the present embodiment is configured by mainly including a capsule-shaped camera body 2 that forms an outside shape, a cover member 3 which is a transparent member provided on an observation window of image pickup means (image pickup section) incorporated in the camera body 2, which is a casing for the camera, a suction cup 4 which is fixing means fitted to the camera body 2 and an abdominal wall fixing section, and a wire 6 that extends from a center of the suction cup 4. The camera 1 is provided with an illumination unit (not shown) that irradiates an object with illumination light.

The camera 1 according to the present embodiment is used for a laparoscopic surgical operation and used to take an image of a treatment region when an organ or the like in an abdominal cavity 101, which is one of body cavities of a patient is treated.

First, the camera 1 is introduced into the abdominal cavity 101 of the patient via a trocar (not shown) punctured through an abdominal wall 102. The wire 6 is hooked onto the camera 1 by a puncture needle (not shown) punctured into the abdominal cavity 101 or the like and pulled out of the body by passing through the abdominal wall 102.

Next, the wire 6 of the camera 1 is passed through a hole 21*a* of a fixing unit 21 prepared on the abdomen side of the patient and pulled toward the abdominal wall 102 side. The wire 6 is then lifted so that the camera 1 comes closer to the abdominal wall 102 and pulled toward the outside of the body until the suction cup 4 sticks fast to the inner surface of the abdominal wall 102. Thus, when the suction cup 4 sticks fast to the abdominal wall 102, the camera 1 is left indwelling and fixed in the abdominal cavity 101.

The fixing unit 21 is provided with a fixing lever 22 that fixes the wire 6 of the camera 1 outside the body. A hole 22*a* through which the wire 6 passes is formed at some midpoint of the fixing lever 22 and the fixing lever 22 is urged in one sideward direction of the fixing unit 21 by a spring 23 provided in the fixing unit 21 so that the position of the hole 22*a* is deviated from the position of the hole 21*a* of the fixing unit 21.

That is, when the user pushes the fixing lever 22 into the fixing unit 21 up to a position at which the hole 21*a* of the fixing unit 21 substantially matches the hole 22*a* of the fixing lever 22 against the urging force of the spring 23, the user can easily pull the wire 6. When the user stops pushing the fixing lever 22 into the fixing unit 21, the fixing lever 22 then slides by receiving the urging force of the spring 23.

Therefore, since the position of the hole 22*a* of the fixing lever 22 deviates from the position of the hole 21*a* of the fixing unit 21, the wire 6 of the camera 1 that passes through the holes 21*a* and 22*a* is sandwiched and fixed in the fixing unit 21. Thus, the camera 1 is left indwelling and fixed in the abdominal cavity 101 in a stable state in which the suction cup 4, which is the abdominal wall fixing section, sticks fast to the abdominal wall 102.

Next, as described above, a more specific configuration of the camera 1 left indwelling and fixed in the body, the abdominal cavity 101 here, will be described in detail using FIG. 3 and FIG. 4 here.

The camera body 2 of the camera 1 includes the aforementioned cover member 3, a control section 5 which constitutes a controller, (here two) batteries 7 which constitute a power supply section, a motor 8 which is drive means (drive source) and constitutes a drive section and an image pickup unit 10 which is image pickup means and constitutes an image pickup section.

The control section 5 is provided with a transmitter that transmits an image signal photoelectrically converted by the image pickup unit 10 to an external device and a receiver (neither one is shown) that receives a drive instruction signal of the motor 8 transmitted from the external device and drives and/or controls the motor 8 according to the received drive instruction signal.

Furthermore, the two batteries 7 constitute a power supply section to drive the control section 5, the motor 8, the image pickup unit 10 and an illumination unit (not shown). The two batteries 7 are electrically connected to the control section 5 via an electric cable (not shown) for a power supply and the control section 5 is provided with communication cables (not shown) individually connected to the motor 8, the image pickup unit 10 or the like for a power supply and signal exchange.

Furthermore, the image pickup unit 10 is configured by including a solid image pickup device 11 such as CCD or CMOS, an image pickup substrate 12 on which the solid image pickup device 11 is mounted, a plurality of objective lenses 13 and a cover lens 14. The image pickup unit 10 outputs a photoelectrically converted image signal to the control section 5. The control section 5 then transmits an image signal from the internal transmitter to a camera control unit (CCU) which is an external device (not shown). An image taken by the image pickup unit 10 is subjected to image processing by the CCU and displayed on an outside monitor (not shown).

The cover member 3 is a transparent member made into a cylindrical shape using acrylic or the like and provided in the camera body 2 so as to be rotatable in an outer circumferential direction. Furthermore, a cylindrical hole 2*a* that rotatably holds the cover member 3 is formed in the camera body 2. To improve the rotatability of the cover member 3, the camera body 2 may also be provided with a bearing or the like to have a configuration that rotatably holds the cover member 3 disposed in the hole 2*a*.

An opening 2*b* is formed in part of the circumference in which the cover member 3 is disposed in the camera body 2. The opening 2*b* is an observation hole for capturing an object image into the image pickup unit 10 and constitutes an observation window. A wiper 15, contamination removing means, is formed at the opening 2*b*, which constitutes a contamination removing section made of an elastic member such as soft rubber so as to contact the outer surface (outer circumferential surface) of the cover member 3, and is disposed so as to be located outside the image taking region of the image pickup unit 10 and fixed.

The position in the longitudinal direction of the wiper 15 is determined so as to be orthogonal to the rotation direction of the cover member 3 and two wipers 15 are disposed in parallel at two opposing edges of the opening 2*b*.

The motor 8 has a rubber roller 9 which is in contact with the inner circumferential surface at one edge of the cover member 3. The roller 9 is provided so as to contact the inner circumferential surface of the cover member 3 with a predetermined contact pressure. The motor 8 is driven/controlled by the control section 5 in response to wireless operation from outside.

The camera 1 of the present embodiment configured as shown above is introduced into the abdominal cavity 101 as shown in FIG. 2 and when the camera 1 is in use by being left indwelling and fixed in the abdominal wall 102, if the motor 8 is driven and the roller 9 is rotated through wireless operation from outside, the cover member 3 in contact with the roller 9 with a predetermined frictional force rotates in the camera body 2. The roller 9 may also be a spur gear, and in this case, such a configuration may be adopted that a gear groove is formed in the inner circumferential surface of the cover member 3 and the cover member 3 rotates in the camera body 2 as the gear rotates.

That is, the cover member 3 rotates in the longitudinal axial direction and the outer circumferential surface thereof comes into sliding contact with the two wipers 15 disposed fixed to the opening 2*b* of the camera body 2 and the wipers 15 thereby wipe deposits off the outer circumferential surface.

Thus, the camera 1 of the present embodiment causes the cover member 3 which is in sliding contact with the two fixed wipers 15 to rotate, and can thereby wipe the outer surface of the cover member 3 exposed from the opening 2b of the camera body 2 with the two wipers 15.

Thus, even if contamination such as mucous membrane, bodily waste, blood or the like and fogging are stuck to the outer surface of the cover member 3, the camera 1 can easily and reliably remove deposits stuck to the cover member 3. Furthermore, the two wipers 15 are fixed in the camera 1 and it is possible to stabilize the contact between the wipers 15 and the cover member 3, and thereby reliably remove deposits stuck to the cover member 3.

By rotating the cover member 3 all the time, the camera 1 can keep the state of the outer surface of the cover member 3 wiped with the two wipers 15. Furthermore, the cover member 3 may be made to rotate in one direction or may be controlled so as to alternately rotate clockwise and counterclockwise.

As described above, the camera 1 of the present embodiment has a configuration in which the transparent cover member 3 is rotated and deposits are removed using the two wipers 15 fixed at the lateral edges of the opening 2b, and the wipers 15 thereby never enter the field of view of the image pickup unit 10 and the image pickup unit 10 can therefore always obtain a clear observation image.

Second Embodiment

Figure 5:
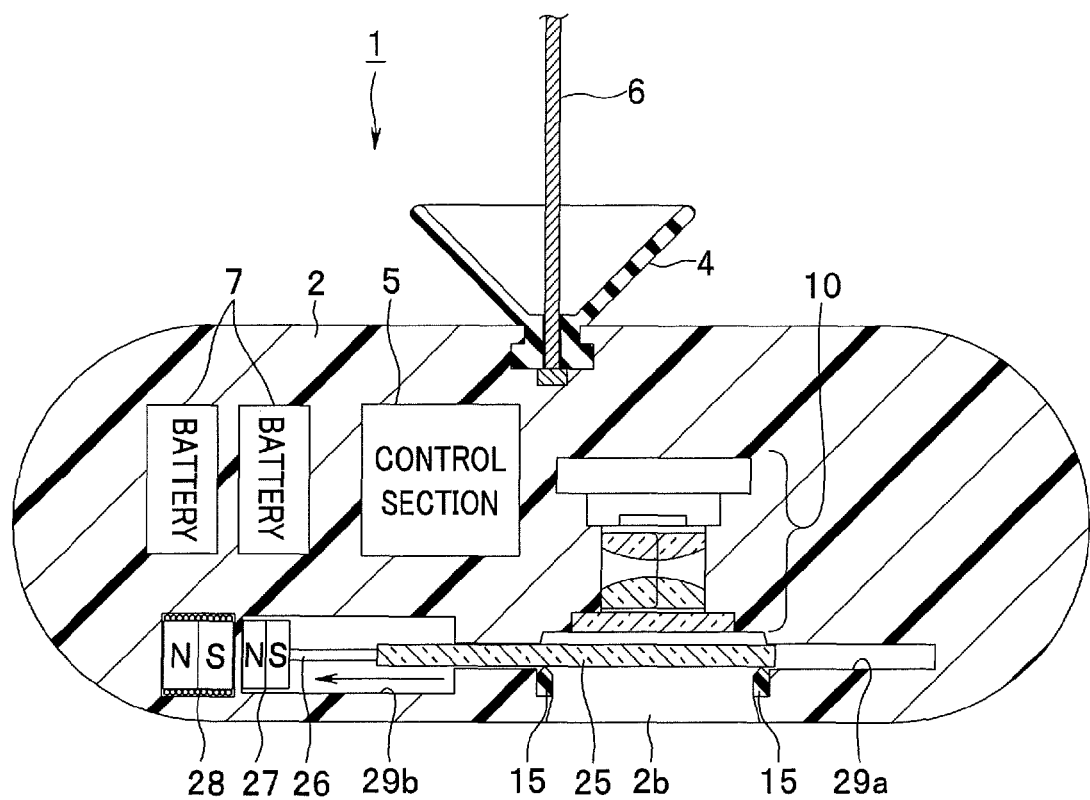
FIG. 5 is a cross-sectional view illustrating a configuration of a camera set up in the abdominal cavity according to a second embodiment of the present invention.
Figure 6:
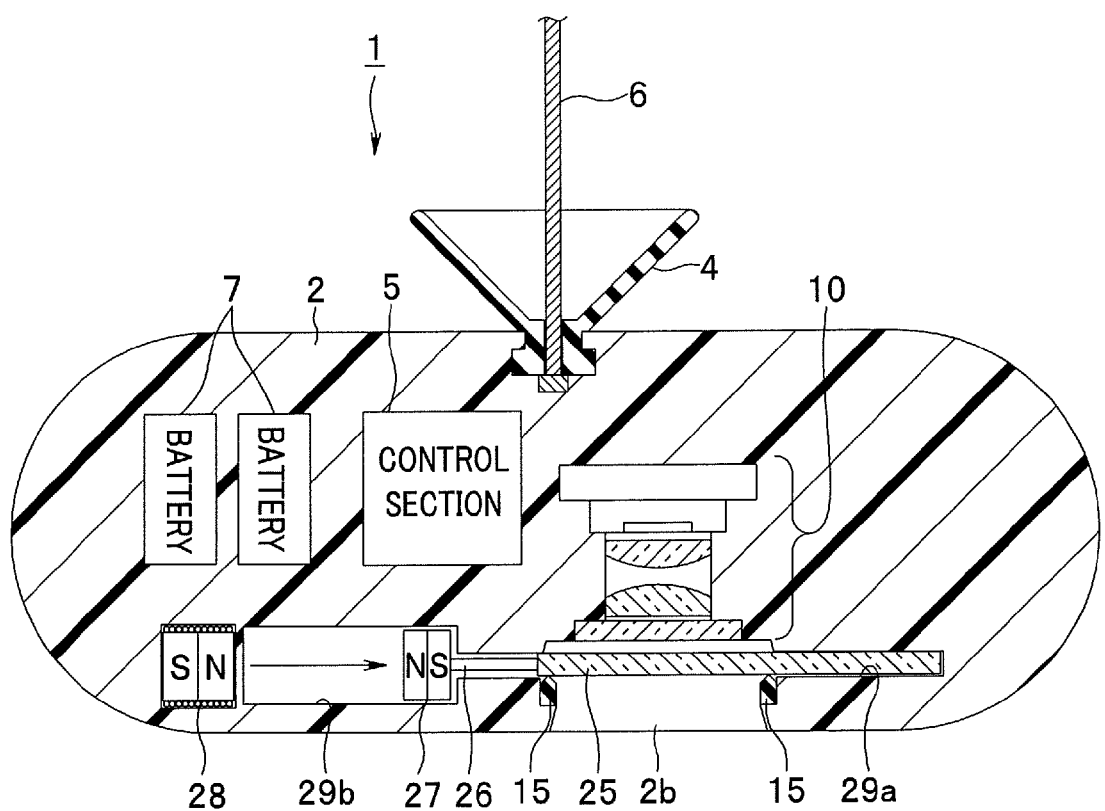
FIG. 6 is a cross-sectional view illustrating the configuration of the camera set up in the abdominal cavity whose cover member has moved sliding from the position in FIG. 5.
Figure 7:
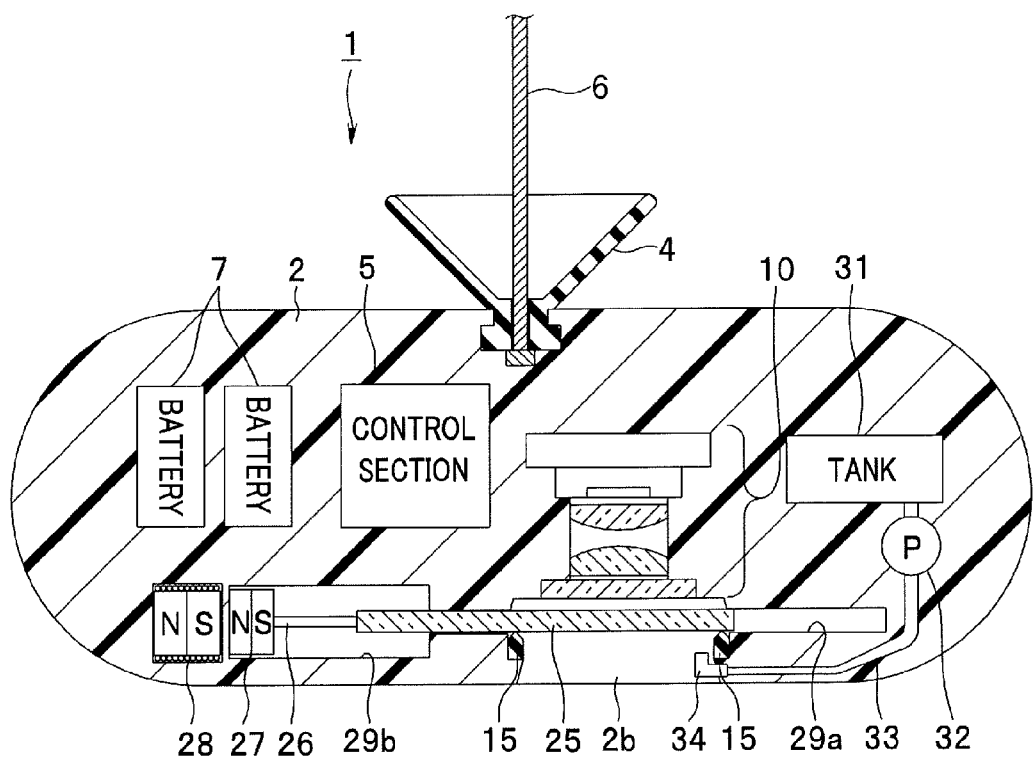
FIG. 7 is a cross-sectional view illustrating a configuration of a camera set up in the abdominal cavity according to a first modification example of the camera set up in the abdominal cavity according to the second embodiment of the present invention.
Figure 8:
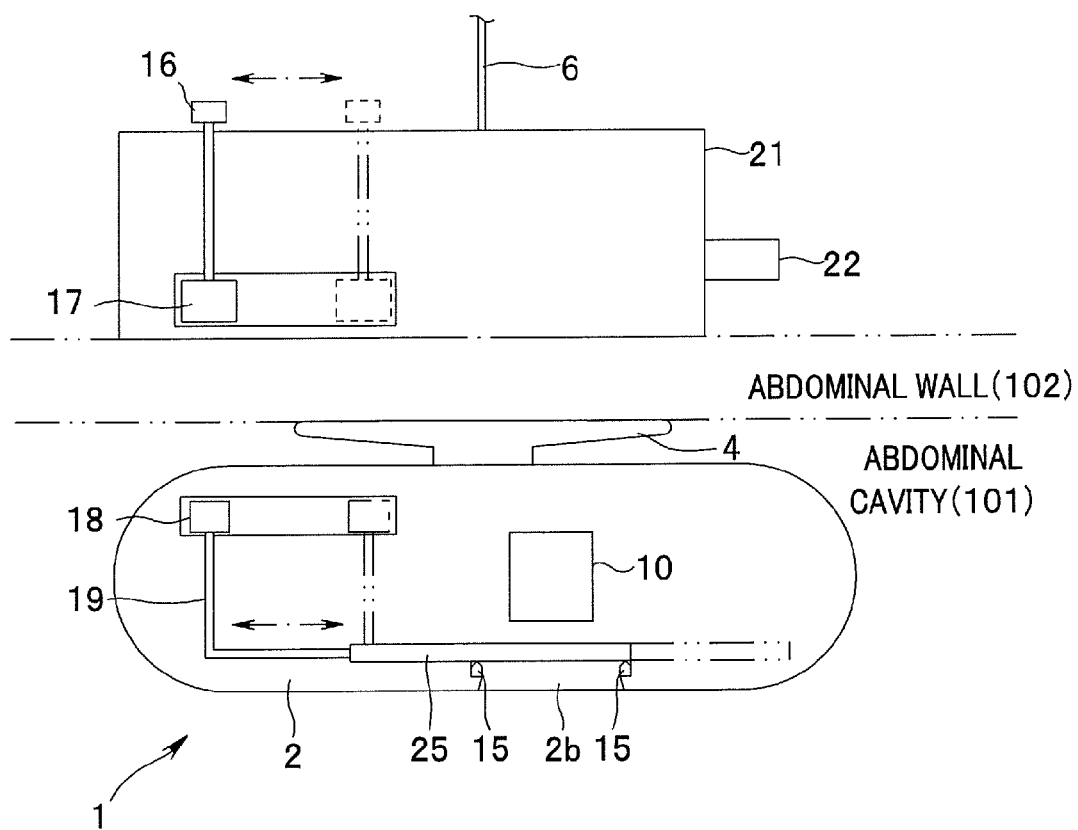
FIG. 8 is a diagram illustrating how a camera according to a second modification example of the camera set up in the abdominal cavity according to the second embodiment of the present invention is set up in the abdominal cavity.

Next, a second embodiment of a camera set up in the abdominal cavity, which is a medical instrument of the present invention, will be described using FIG. 5 to FIG. 8 below. FIG. 5 to FIG. 8 are related to the second embodiment of the present invention, FIG. 5 is a cross-sectional view illustrating a configuration of the camera set up in the abdominal cavity, FIG. 6 is a cross-sectional view illustrating the configuration of the camera set up in the abdominal cavity whose cover member has moved sliding from the position in FIG. 5, FIG. 7 is a cross-sectional view illustrating a configuration of a camera set up in the abdominal cavity according to a first modification example and FIG. 8 is a diagram illustrating how a camera set up in the abdominal cavity according to a second modification example is set up in the abdominal cavity. In the following descriptions, the same components as those in the camera set up in the abdominal cavity of the first embodiment will be assigned the same reference numerals and descriptions of those components and operations and/or effects will be omitted.

The camera 1 of the present embodiment has a configuration including a tabular cover member 25 instead of the cylindrical cover member 3 according to the first embodiment.

To be more specific, as shown in FIG. 5 and FIG. 6, a groove 29a is formed in the camera body 2 of the camera 1 so that the tabular cover member 25 can be slidably disposed. The groove 29a is formed so that the cover member 25 covers the opening 2b, which is an observation window for the image pickup unit 10 to capture an object image and guides the sliding cover member 25 in a rectilinear direction. The cover member 25 is disposed in the groove 29a so that the outer surface thereof contacts the two wipers 15 provided at the opening 2b.

One side of the cover member 25 disposed in the groove 29a is connected to one end of the shaft body 26. Furthermore, a magnet (permanent magnet) 27 is provided at the other end of the shaft body 26. The magnet 27 is slidably disposed in a cavity 29b formed in communication with the groove 29a formed in the camera body 2.

Furthermore, the camera body 2 is provided with an electromagnet 28 at an end of the cavity 29b. The electromagnet 28 is electrically connected to the control section 5 and switching between the S pole and N pole is controlled by the control section 5.

In the camera 1 of the present embodiment configured as shown above, the control section 5 controls switching between the S pole and N pole of the electromagnet 28 based on wireless operation from outside. That is, in the camera 1, the magnet 27 connected to the cover member 25 via the shaft body 26 is given an attractive force or repulsive force by the electromagnet 28 through the control of switching between unlike poles (see FIG. 5) or like poles (see FIG. 6) of the electromagnet 28. The action of the attractive force and repulsive force of the magnetic force causes the cover member 25 to move sliding along the groove 29a. That is, the camera 1 according to the present embodiment has a configuration in which the drive section (drive means/drive source) causes the cover member 25 to move sliding along the groove 29a through the magnetic action between the magnet 27 and the electromagnet 28.

Thus, when the cover member 25 moves sliding along the groove 29a, the outer surface thereof makes a sliding contact with the two wipers 15. Therefore, the camera 1 can wipe the outer surface of the cover member 25 exposed from the opening 2b of the camera body 2 with the two wipers 15.

As described above, in the camera 1 of the present embodiment as in the case of the first embodiment, even if contamination such as mucous membrane, bodily waste, blood or the like and fogging are stuck to the outer surface of the tabular cover member 25, the cover member 25 moves while making a sliding contact with the two wipers 15 fixed to the opening 2b, and it is thereby possible to easily, reliably and stably remove deposits stuck to the cover member 25.

In the present embodiment, when the camera 1 is in use, the electromagnet 28 may be driven as appropriate only when deposits are stuck to the cover member 25 to remove the deposits stuck to the cover member 25 or switching control over the electromagnet 28 may be always performed so as to cause the cover member 25 to always slide.

As described above, as in the case of the first embodiment, the camera 1 of the present embodiment also adopts a configuration in which the transparent cover member 25 is made to move sliding, and deposits are easily and reliably removed using the two wipers 15 fixed at the lateral edges of the opening 2b, and the wipers 15 thereby also never enter the field of view of the image pickup unit 10, and the image pickup unit 10 can therefore always obtain a clear observation image.

Furthermore, since the cover member 25 is tabular-shaped, the cover member 25 can be formed of sapphire glass in addition to acrylic or the like. When the cover member 25 is formed of sapphire glass, the camera 1 can be configured to have autoclave resistance whereby sterilization/disinfection is performed under high pressure and high temperature.

First Modification Example

As shown in FIG. 7, the camera 1 may be provided with a tank 31 that stores a cleaning liquid or defogging liquid and a micro pump 32 that jets the liquid in the tank 31 over the outer surface of the cover member 25 exposed from the opening 2b.

The micro pump 32 is also driven/controlled by the control section 5 based on wireless operation from outside. The liquid in the tank 31 is jetted over the outer surface of the cover member 25 via a liquid sending tube 33 with the micro pump 32 interposed in between and a nozzle 34 provided at the opening 2b.

Thus, by causing the cleaning liquid or defogging liquid to be jetted over the outer surface of the cover member 25 exposed from the opening 2b, the camera 1 can efficiently remove deposits of the cover member 25 and prevent fogging of the outer surface of the cover member 25.

Second Modification Example

As shown in FIG. 8, a configuration may be adopted in which the fixing unit 21 is provided with a magnet (permanent magnet) 17 that is manually made to slide and the cover member 25 is made to slide following the movement of the magnet 17.

To be more specific, the magnet 17 provided inside the fixing unit 21 is connected to a lever 16 and the lever 16 is operated to slide. Furthermore, the cover member 25 slidably disposed in the camera body 2 of the camera 1 is connected to a magnet 18 and a bar-shaped support body 19 which is L-shaped here. The magnet 17 of the fixing unit 21 and the magnet 18 of the camera 1 are arranged so that unlike poles face each other, whereby an action of attracting each other works.

Thus, in the camera 1 of the present modification example, when the lever 16 of the fixing unit 21 is operated to slide, the magnet 18 in the camera body 2 follows the moving magnet 17 and the cover member 25 moves sliding while making a sliding contact with the two wipers 15 fixed at the lateral edges of the opening 2b. Deposits stuck to the cover member 25 are thereby removed.

Third Embodiment

Figure 9:
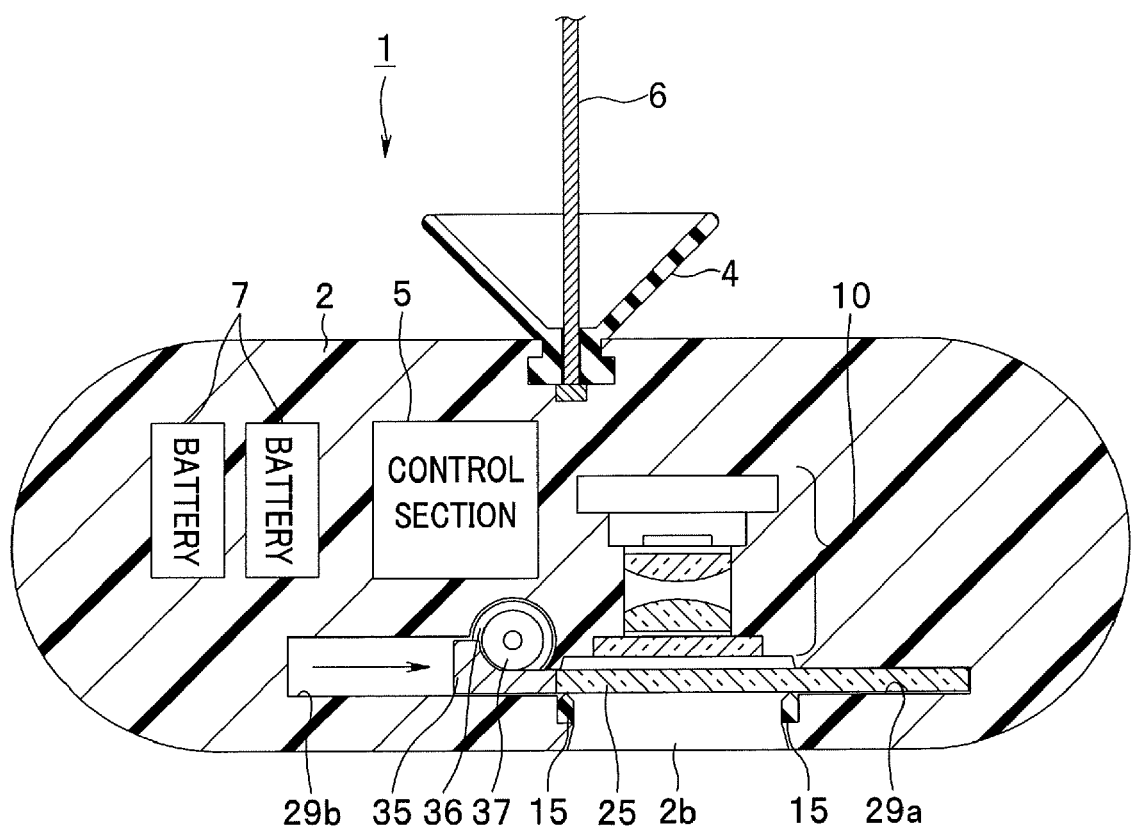
FIG. 9 is a cross-sectional view illustrating a configuration of a camera set up in the abdominal cavity according to a third embodiment of the present invention.
Figure 10:
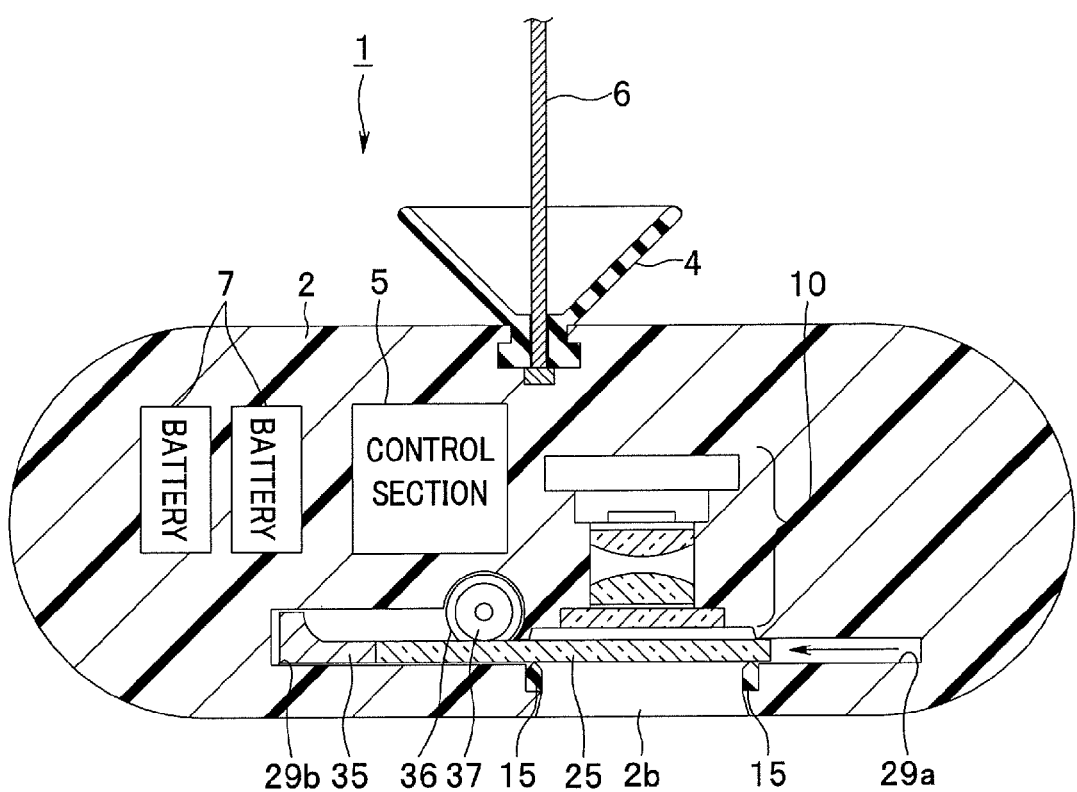
FIG. 10 is a cross-sectional view illustrating the configuration of the camera set up in the abdominal cavity according to the third embodiment of the present invention whose cover member has moved sliding from the position in FIG. 9.

Next, a third embodiment of a camera set up in the abdominal cavity, which is a medical instrument according to the present invention, will be described using FIG. 9 and FIG. 10 below. FIG. 9 and FIG. 10 are related to the third embodiment of the present invention, FIG. 9 is cross-sectional view illustrating a configuration of the camera set up in the abdominal cavity and FIG. 10 is a cross-sectional view illustrating a configuration of the camera set up in the abdominal cavity whose cover member has moved sliding from the position in FIG. 9. In the following descriptions, the same components as those in the camera set up in the abdominal cavity of the first embodiment and the second embodiment will be assigned the same reference numerals and descriptions of those components and operations and/or effects will be omitted.

As in the case of the second embodiment, the camera 1 of the present embodiment shown in FIG. 9 and FIG. 10 is configured to include the tabular cover member 25 that moves sliding along the groove 29a formed in the camera body 2. A motor 36 is used for the drive section (drive means/drive source) that moves the cover member 25 sliding along the groove 29a.

The cover member 25 is connected to a stopper member 35 in which a quasi-tabular protruding section whose end protrudes upward is formed on one side. The stopper member 35 is shaped so as to be slidable in the cavity 29b formed in the camera body 2.

The motor 36 has a rubber roller 37 that contacts the top surfaces of the cover member 25 and the stopper member 35. The roller 37 is provided so as to contact the top surfaces of the cover member 25 and the stopper member 35 with a predetermined contact pressure.

Furthermore, the motor 36, which is a drive section, is also driven/controlled by the control section 5 in response to wireless operation from outside. The motor 36 is incorporated in the camera body 2 so that the cover member 25 moves sliding along the groove 29a as the roller 37 rotates and the rotation axis of the roller 37 is disposed in a direction orthogonal to the moving direction of the cover member 25.

Furthermore, the protruding portion that protrudes upward contacts the roller 37 and the stopper member 35 thereby regulates one sliding position of the connected cover member 25.

In the camera 1 configured as described above, when the rotation direction of the motor 36 is changed alternately under the control of the control section 5, the cover member 25 which is led out by the contact with the roller 37 moves sliding along the groove 29a. Therefore, the camera 1 can wipe the outer surface of the cover member 25 exposed from the opening 2b of the camera body 2 using the two fixed wipers 15.

As described above, the camera 1 of the present embodiment also has effects similar to those of the second embodiment, the transparent cover member 25 is made to move sliding, deposits can be easily and reliably removed by the two fixed wipers 15, and moreover, the wipers 15 never enter the field of view of the image pickup unit 10, and the image pickup unit 10 can therefore always obtain a clear observation image.

Here, the tabular cover member 25 can also be formed of sapphire glass, and the camera 1 can be thereby configured to have autoclave resistance whereby sterilization/disinfection is performed under high pressure and high temperature.

Fourth Embodiment

Figure 11:
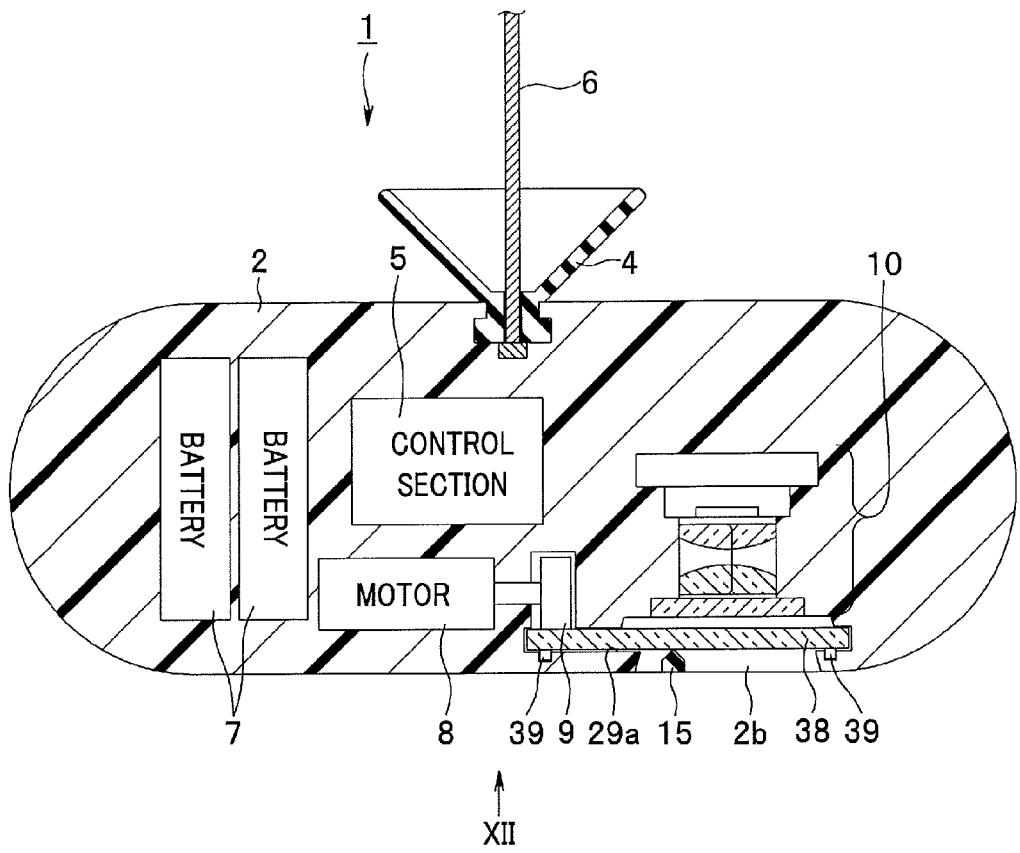
FIG. 11 is a cross-sectional view illustrating a configuration of a camera set up in the abdominal cavity according to a fourth embodiment of the present invention.
Figure 12:
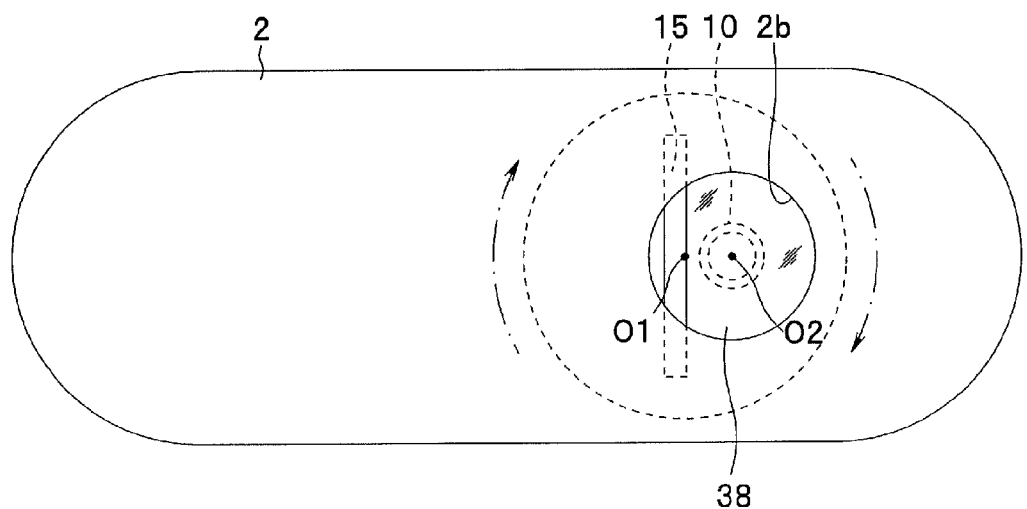
FIG. 12 is a plan view of the camera set up in the abdominal cavity according to the fourth embodiment of the present invention in FIG. 11 viewed from a direction indicated by an arrow XII.

Next, a fourth embodiment of a camera set up in the abdominal cavity, which is a medical instrument of the present invention, will be described below using FIG. 11 and FIG. 12. FIG. 11 and FIG. 12 are related to the fourth embodiment of the present invention, FIG. 11 is a cross-sectional view illustrating a configuration of the camera set up in the abdominal cavity and FIG. 12 is a plan view of the camera set up in the abdominal cavity in FIG. 11 viewed from a direction indicated by an arrow XII. In the following descriptions, the same components as those in the camera set up in the abdominal cavity of the first embodiment will be assigned the same reference numerals and descriptions of those components and operations and/or effects will be omitted.

In the camera 1 of the present embodiment shown in FIG. 11 and FIG. 12, a disk-shaped transparent cover member 38 is rotatably disposed in the groove 29a of the camera body 2."

The cover member 38 is held in contact with a plurality of small rollers 39 disposed around the opening 2b of the camera body 2 on the edge of the underside thereof and disposed so as to be able to smoothly rotate around a center O1 along the outer circumferential direction of the opening 2b.

Furthermore, the cover member 38 is provided so that the edge of the top surface contacts the roller 9 of the motor 8, which is a drive section (drive means/drive source), with a predetermined contact pressure. That is, the motor 8 causes the roller 9 to rotate and thereby causes the cover member 38 in contact with the roller 9 to rotate around the center O1. Furthermore, the cover member 38 is provided so that the center O1 thereof is located at a position different from a center O2 of the image pickup unit 10.

The wiper 15 is fixedly disposed in the camera body 2 so as to contact the outer surface of the cover member 38 and lie laterally across the opening 2b. The wiper 15 is disposed at a position where the wiper 15 does not enter the field of view of the image pickup unit 10 and a position including the center O1 of the cover member 38.

In the camera 1 configured as shown above as in the case of the first embodiment, the roller 9 of the motor 8 also rotates under the control of the control section 5. Thus, the disk-shaped cover member 38 rotates around the center O1 by receiving the rotation force of the roller 9 in contact. In the camera 1, the outer surface of the cover member 38 exposed from the opening 2b of the camera body 2 is wiped with the fixed wiper 15.

As described above, the camera 1 of the present embodiment also exerts effects similar to those of the above described embodiments, causes the transparent disk-shaped cover member 38 to rotate, and can thereby easily and reliably remove deposits using the fixed wiper 15, and moreover the wiper 15 never enters the field of view of the image pickup unit 10, and the image pickup unit 10 can therefore always obtain a clear observation image.

Since the disk-shaped cover member 38 can also be formed of sapphire glass here, the camera 1 can be configured to have autoclave resistance whereby sterilization/disinfection is performed under high pressure and high temperature.

Fifth Embodiment

Figure 13:
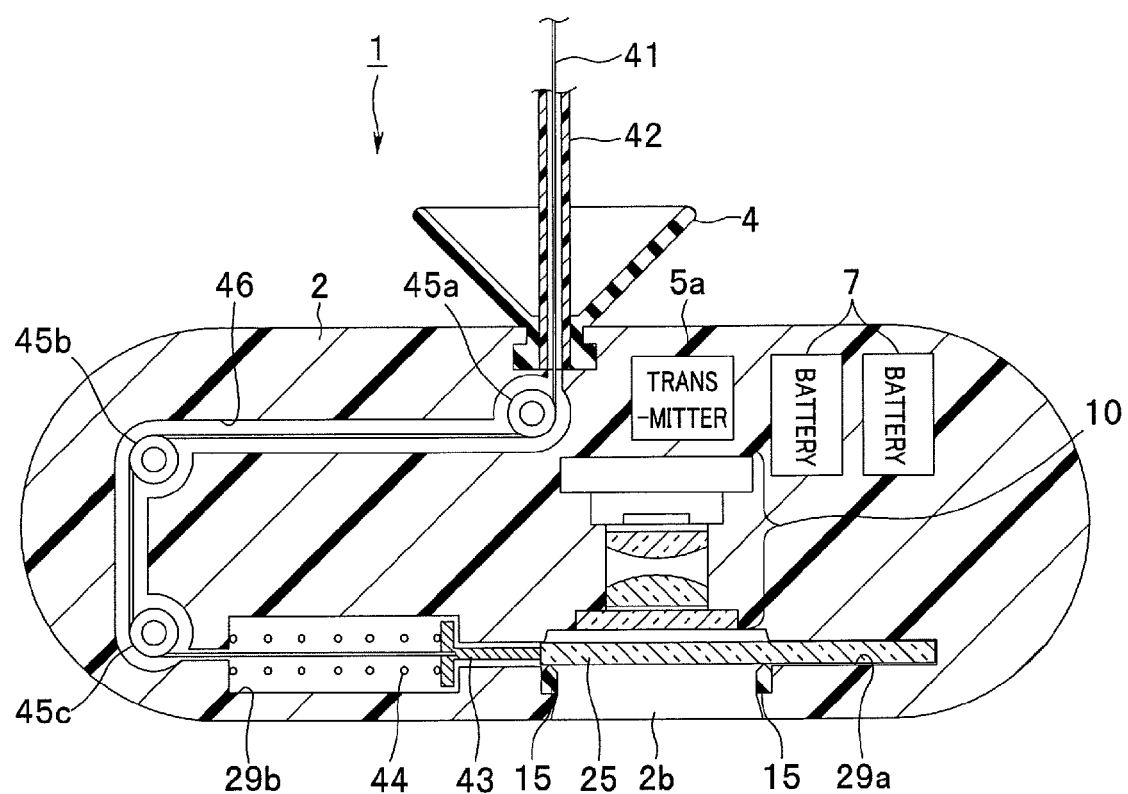
FIG. 13 is a cross-sectional view illustrating a configuration of a camera set up in the abdominal cavity according to a fifth embodiment of the present invention.
Figure 14:
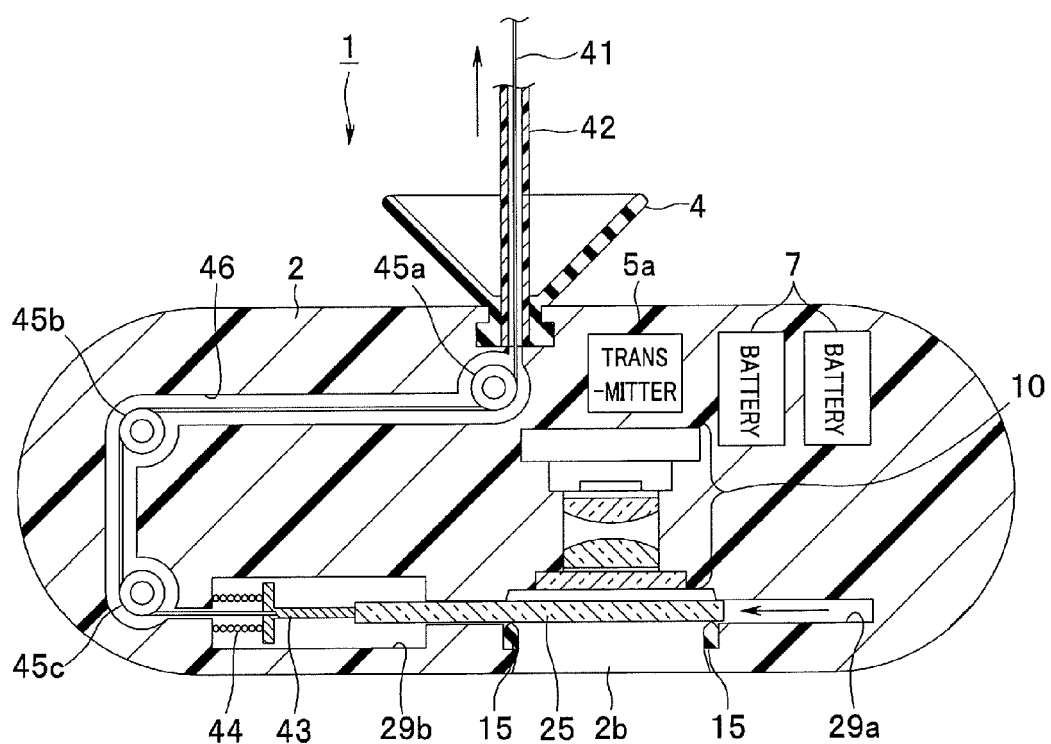
FIG. 14 is a cross-sectional view illustrating the configuration of the camera set up in the abdominal cavity according to the fifth embodiment of the present invention whose cover member has moved sliding from the position in FIG. 13.
Figure 15:
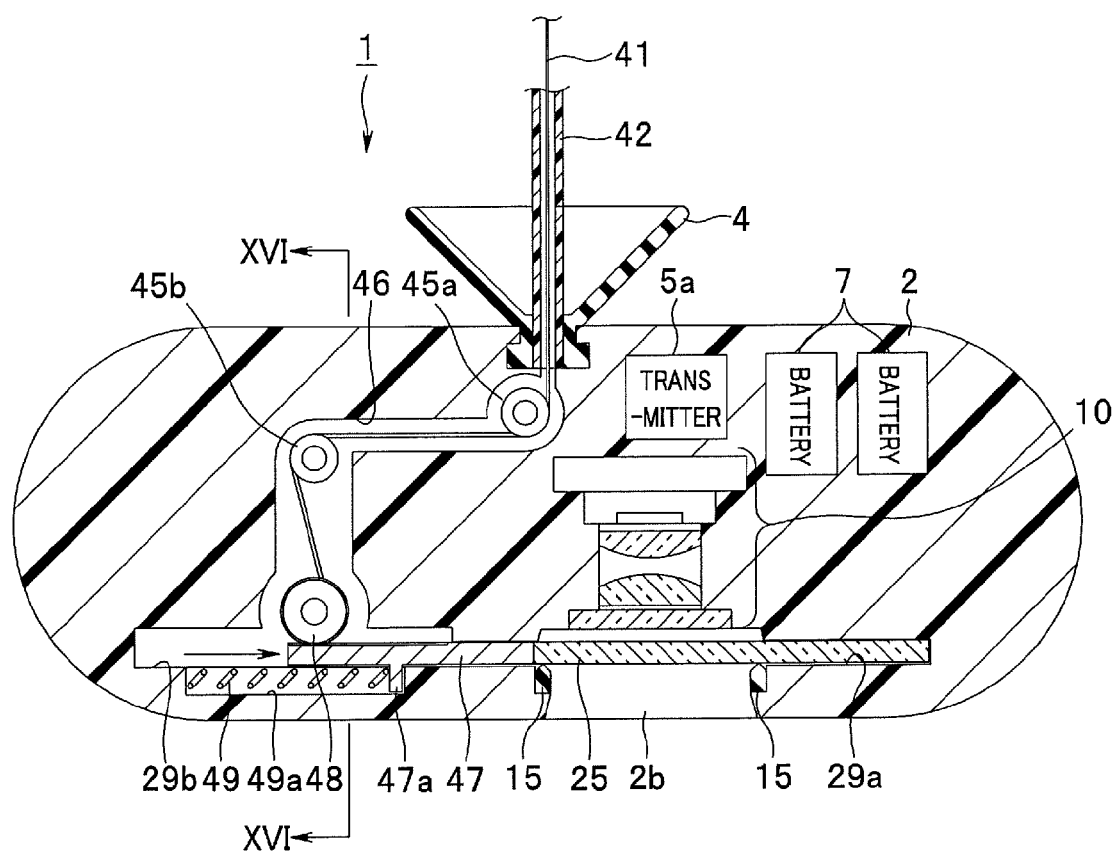
FIG. 15 is a cross-sectional view illustrating a configuration of a camera set up in the abdominal cavity according to a modification example of the camera set up in the abdominal cavity according to the fifth embodiment of the present invention.
Figure 16:
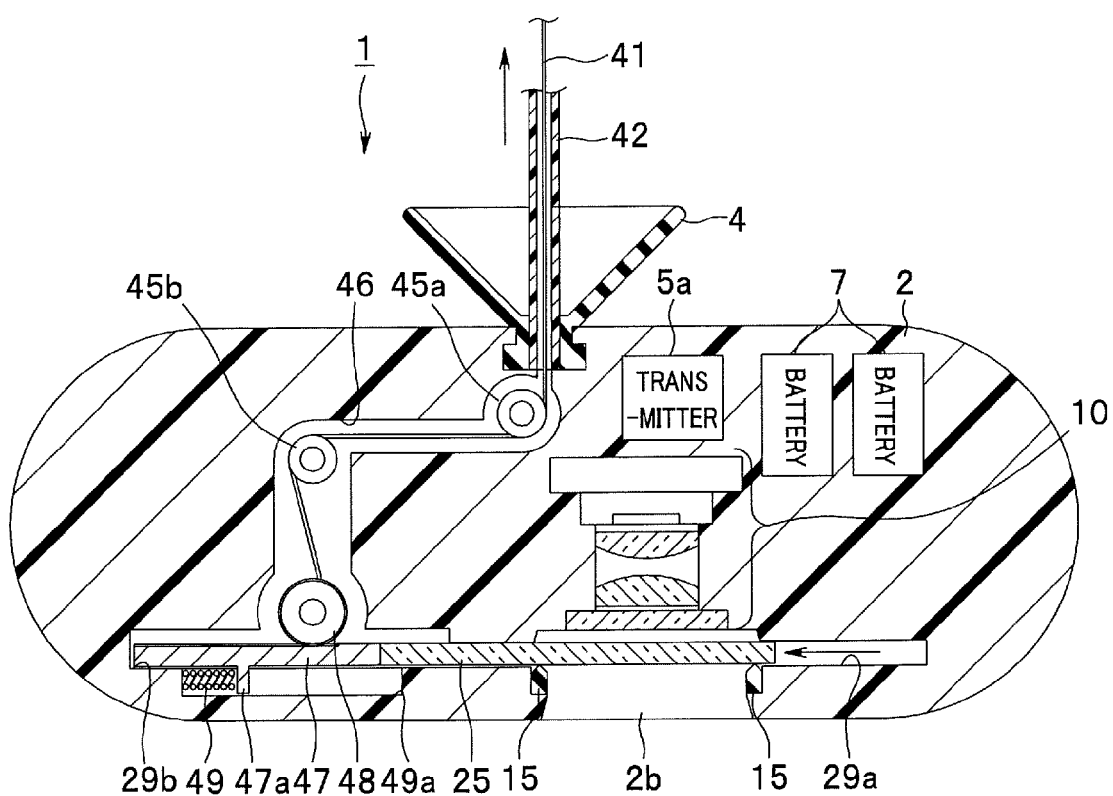
FIG. 16 is a cross-sectional view illustrating a configuration of the camera set up in the abdominal cavity according to the modification example of the camera set up in the abdominal cavity according to the fifth embodiment of the present invention whose cover member has moved sliding from the position in FIG. 15.
Figure 17:
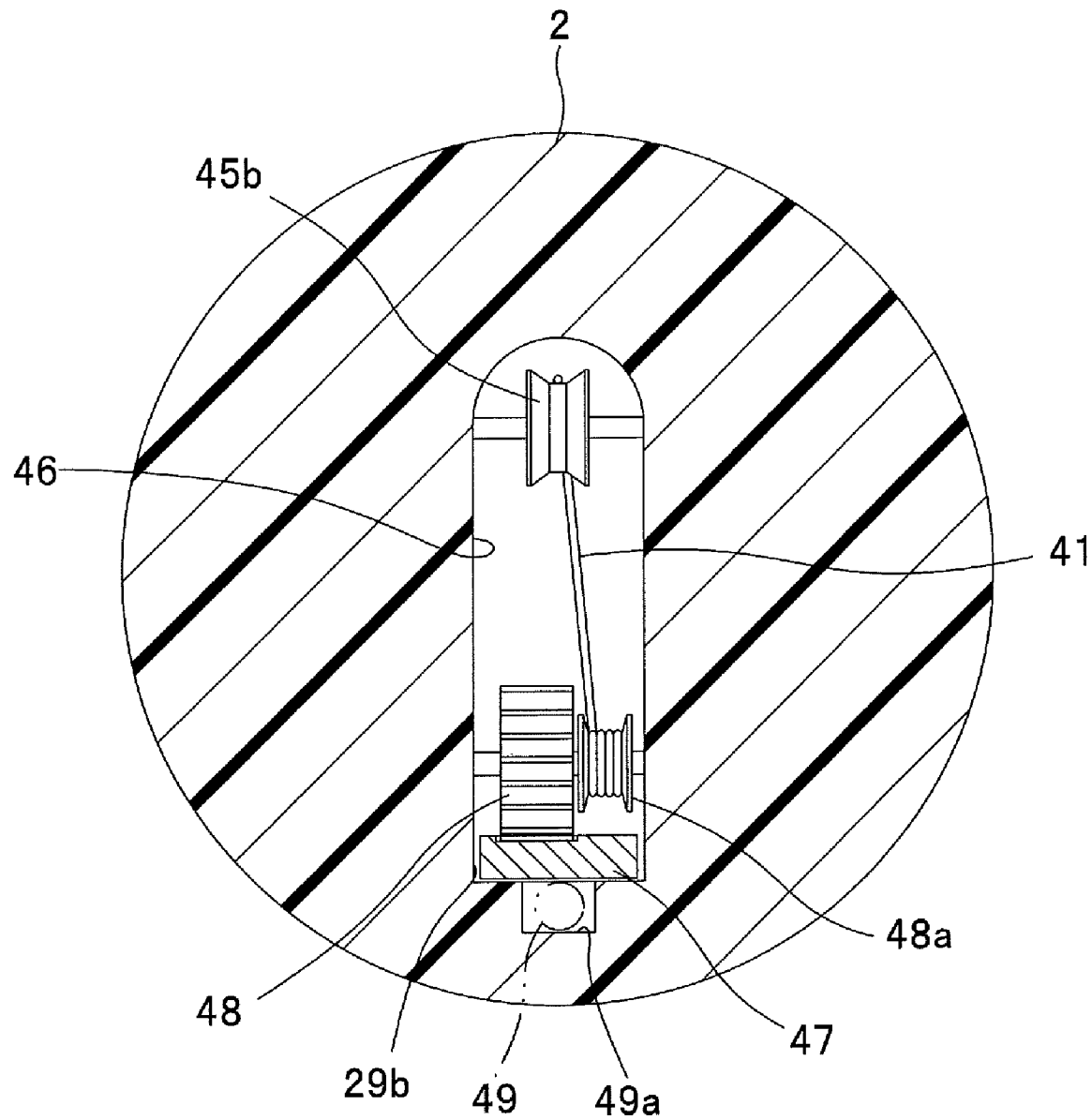
FIG. 17 is a cross-sectional view along a line XVII-XVII in FIG. 16 of the camera set up in the abdominal cavity according to the modification example of the camera set up in the abdominal cavity according to the fifth embodiment of the present invention.

Next, a fifth embodiment of a camera set up in the abdominal cavity, which is a medical instrument according to the present invention, will be described below using FIG. 13 to FIG. 17. FIG. 13 to FIG. 17 are related to the fifth embodiment of the present invention, FIG. 13 is a cross-sectional view illustrating a configuration of the camera set up in the abdominal cavity, FIG. 14 is a cross-sectional view illustrating the configuration of the camera set up in the abdominal cavity whose cover member has moved sliding from the position in FIG. 13, FIG. 15 is a cross-sectional view illustrating a configuration of a camera set up in the abdominal cavity according to a modification example, FIG. 16 is a cross-sectional view illustrating a configuration of the camera set up in the abdominal cavity whose cover member has moved sliding from the position in FIG. 15 and FIG. 17 is a cross-sectional view along a line XVII-XVII in FIG. 16. In the following descriptions, the same components as those in the camera set up in the abdominal cavity of the first to fourth embodiments will be assigned the same reference numerals and descriptions of those components and operations and/or effects will be omitted.

The camera 1 of the present embodiment shown in FIG. 13 and FIG. 14 is configured such that the drive configuration in which the tabular cover member 25 is made to move sliding along the groove 29a of the camera body 2 can be realized not electrodynamically as in the above described embodiments but manually by pulling or slackening an operation wire 41 that extends from the suction cup 4.

To be more specific, in the camera 1, as in the cases of the second and third embodiments, the tabular cover member 25 is slidably disposed in the groove 29a of the camera body 2. One side of the cover member 25 is connected to a shaft body 43 in which the outward flange is formed.

The outward flange part of the shaft body 43 is accommodated in the cavity 29b and urged in one direction by an urging force of a compression coil spring 44 provided in the cavity 29b. Furthermore, one end of the operation wire 41 is connected to the shaft body 43.

The operation wire 41 is inserted into a tubular body 42 that extends from the suction cup 4 and disposed in a wire insertion path 46 formed in the camera body 2. The tubular body 42 is designed to be sandwiched by the fixing unit 21 (see FIG. 2) when the camera 1 is left indwelling and fixed in the abdominal wall 102 to allow the operation wire 41 to be freely pulled or slackened.

The wire insertion path 46 is provided with three pulleys 45a, 45b and 45c to change the arrangement direction of the operation wire 41.

The camera 1 of the present embodiment is provided with a transmitter 5a that transmits an image signal photoelectrically converted by the image pickup unit 10 to a camera control unit (CCU) which is an external device (not shown).

When the user pulls the operation wire 41, the camera 1 configured as shown above can move the cover member 25 sliding along the groove 29a of the camera body 2 in one direction together with the shaft body 43 against the urging force of the compression coil spring 44. Furthermore, when the user slackens the pulled operation wire 41, the shaft body 43 is pushed by the urging force of the compression coil spring 44 and the cover member 25 moves sliding along the groove 29a of the camera body 2 in the other direction. Thus, in the camera 1, the outer surface of the cover member 25 exposed from the opening 2b of the camera body 2 is wiped with the two fixed wipers 15.

As described above, as in the case of the above described embodiment, the camera 1 of the present embodiment has a configuration in which the transparent cover member 25 is made to move sliding so as to allow the two fixed wipers 15 at the lateral edges of the opening 2b to easily and reliably remove deposits of the cover member 25, and the wipers 15 thereby never enter the field of view of the image pickup unit 10 here, and the image pickup unit 10 can therefore always obtain a clear observation image.

Furthermore, since tabular cover member 25 can also be formed of sapphire glass here, the camera 1 can be configured here to have autoclave resistance whereby sterilization/disinfection is performed under high pressure and high temperature.

The above described configuration of the camera 1 in which the cover member 25 is made to move sliding along the groove 29a of the camera body 2 by pulling/slackening the operation wire 41 in one direction may also be realized using a rack and pinion mechanism shown in FIG. 15 to FIG. 17.

To be more specific, as shown in FIG. 15 to FIG. 17, the camera 1 has a rack 47 connected to one side of the cover member 25 and a pinion 48 that meshes with the rack 47.

The rack 47 has a protrusion 47a that extends downward. The rack 47 is urged in one direction by a compression coil spring 49 disposed in contact with the protrusion 47a. The compression coil spring 49 is accommodated in a concave section 49a formed below the cavity 29b.

The pinion 48 is connected and fixed to a pulley 48a around which the operation wire 41 is wound on the same rotation shaft and rotatably supported in the camera body 2 (see FIG. 17). That is, such a configured is adopted that when the operation wire 41 is pulled, the pulley 48a is given a rotation force and the pinion 48 rotates in one direction.

Thus, when the operation wire 41 is pulled and the pinion 48 rotates in one direction, the rack 47 that meshes with the pinion 48 moves in one direction against the urging force of the compression coil spring 49. Thus, the cover member 25 also moves sliding along the groove 29a of the camera body 2 in one direction.

Furthermore, when the pulled operation wire 41 is slackened, the rack 47 moves in the other direction by receiving the urging force of the compression coil spring 49 and the cover member 25 also moves sliding along the groove 29a of the camera body 2 in the other direction. In this case, the pinion 48 rotates in accordance with the movement of the rack 47 and the operation wire 41 is wound around the pulley 48a.

The camera 1 in such a configuration can cause the transparent cover member 25 to move sliding through the pulling/slackening operation of the operation wire 41 to allow the two wipers 15 to easily and reliably remove deposits of the cover member 25 and exert the aforementioned effects.

Sixth Embodiment

Figure 18:
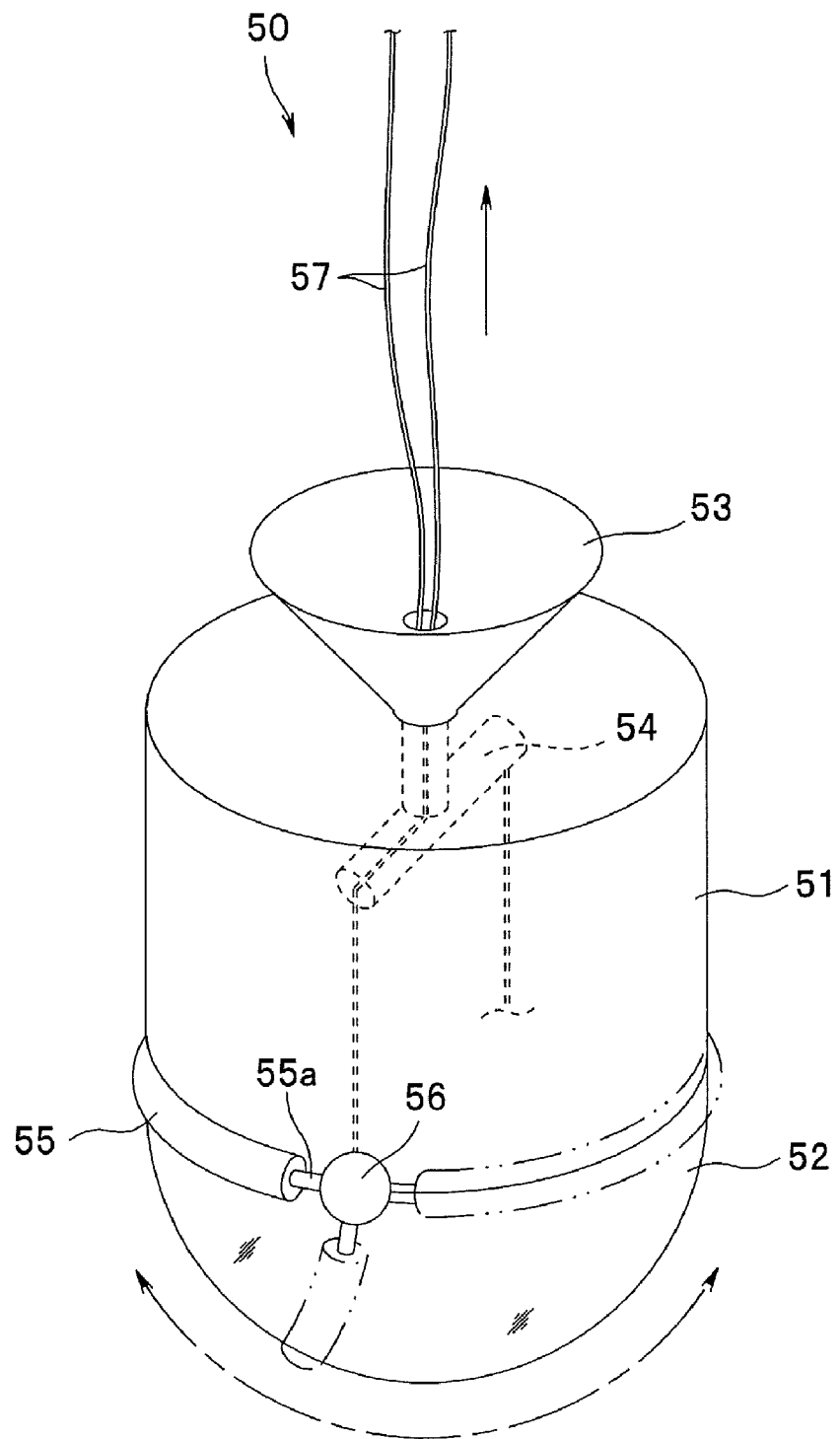
FIG. 18 is a perspective view illustrating a configuration of a camera set up in the abdominal cavity according to a sixth embodiment of the present invention.
Figure 19:
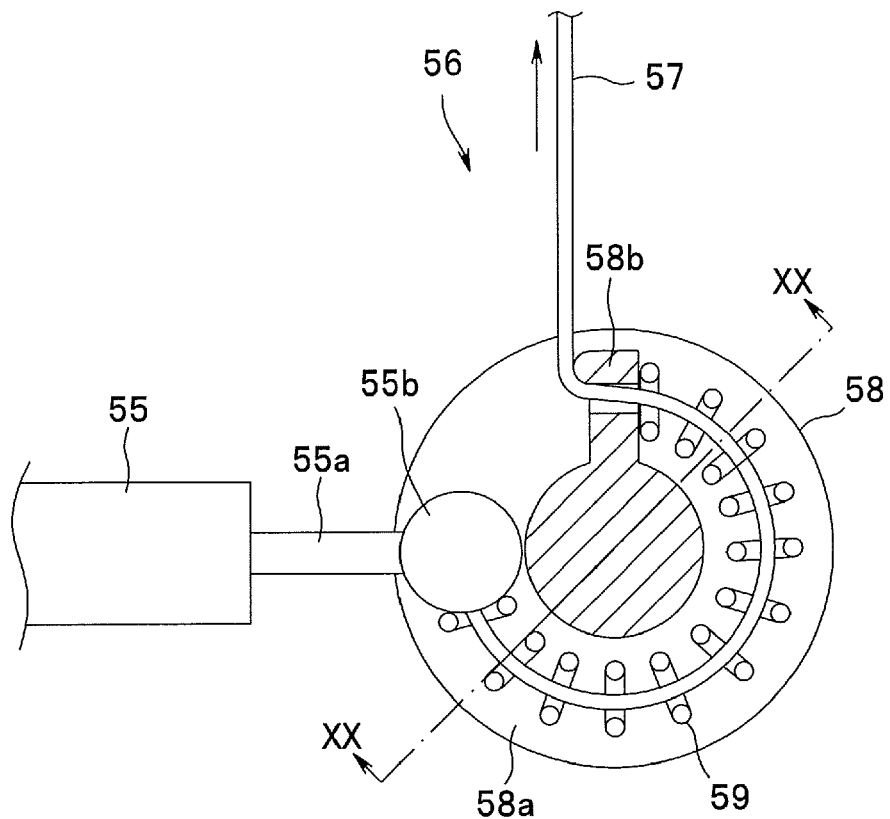
FIG. 19 is a cross-sectional view illustrating a configuration of a rotation mechanism that rotates a wiper of the camera set up in the abdominal cavity according to the sixth embodiment of the present invention.
Figure 20:
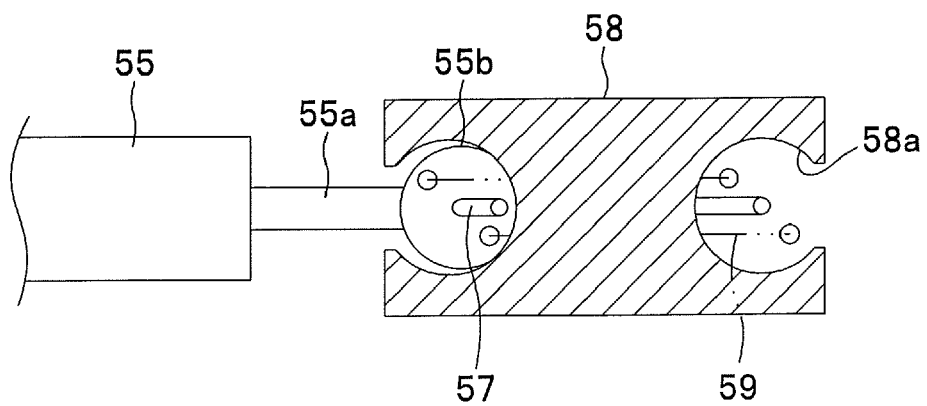
FIG. 20 is a cross-sectional view along a line XX-XX in FIG. 19 of the camera set up in the abdominal cavity according to the sixth embodiment of the present invention.
Figure 21:
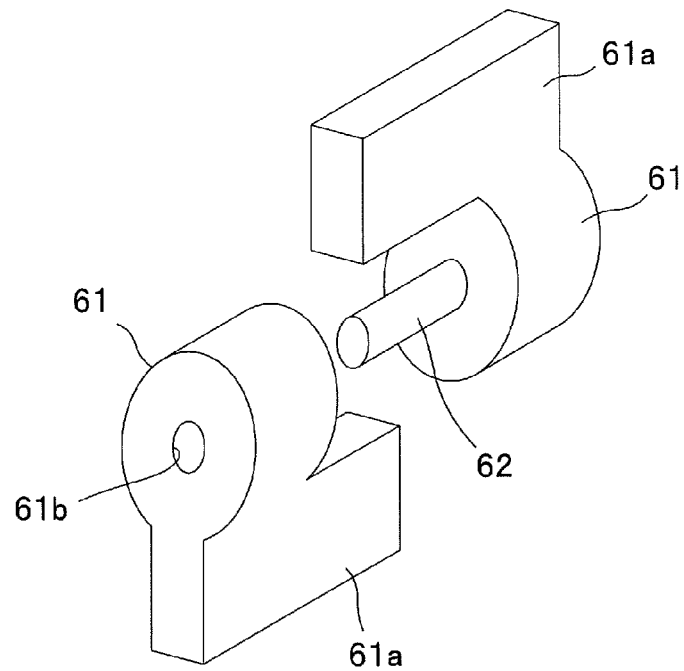
FIG. 21 is an exploded perspective view illustrating a configuration of a rotation mechanism that rotates a wiper according to a modification example of the camera set up in the abdominal cavity according to the sixth embodiment of the present invention.
Figure 22:
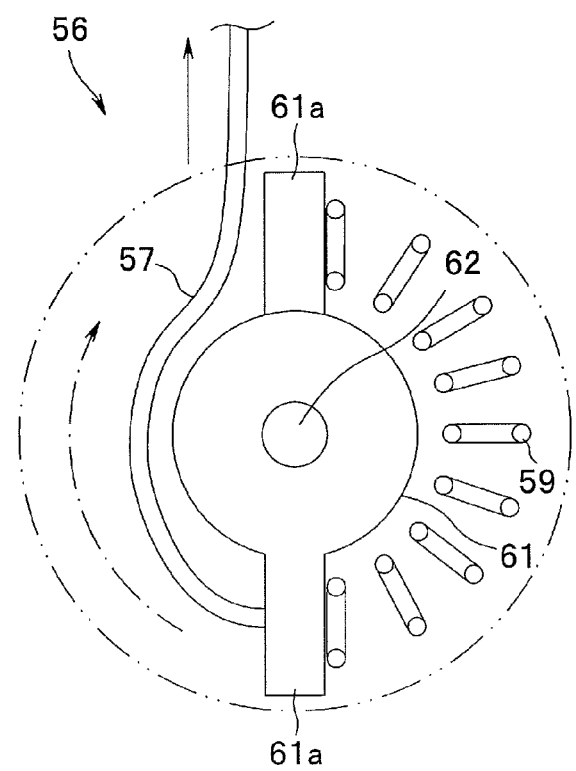
FIG. 22 is a side view illustrating a configuration of the rotation mechanism in FIG. 21 according to the modification example of the camera set up in the abdominal cavity according to the sixth embodiment of the present invention.
Figure 23:
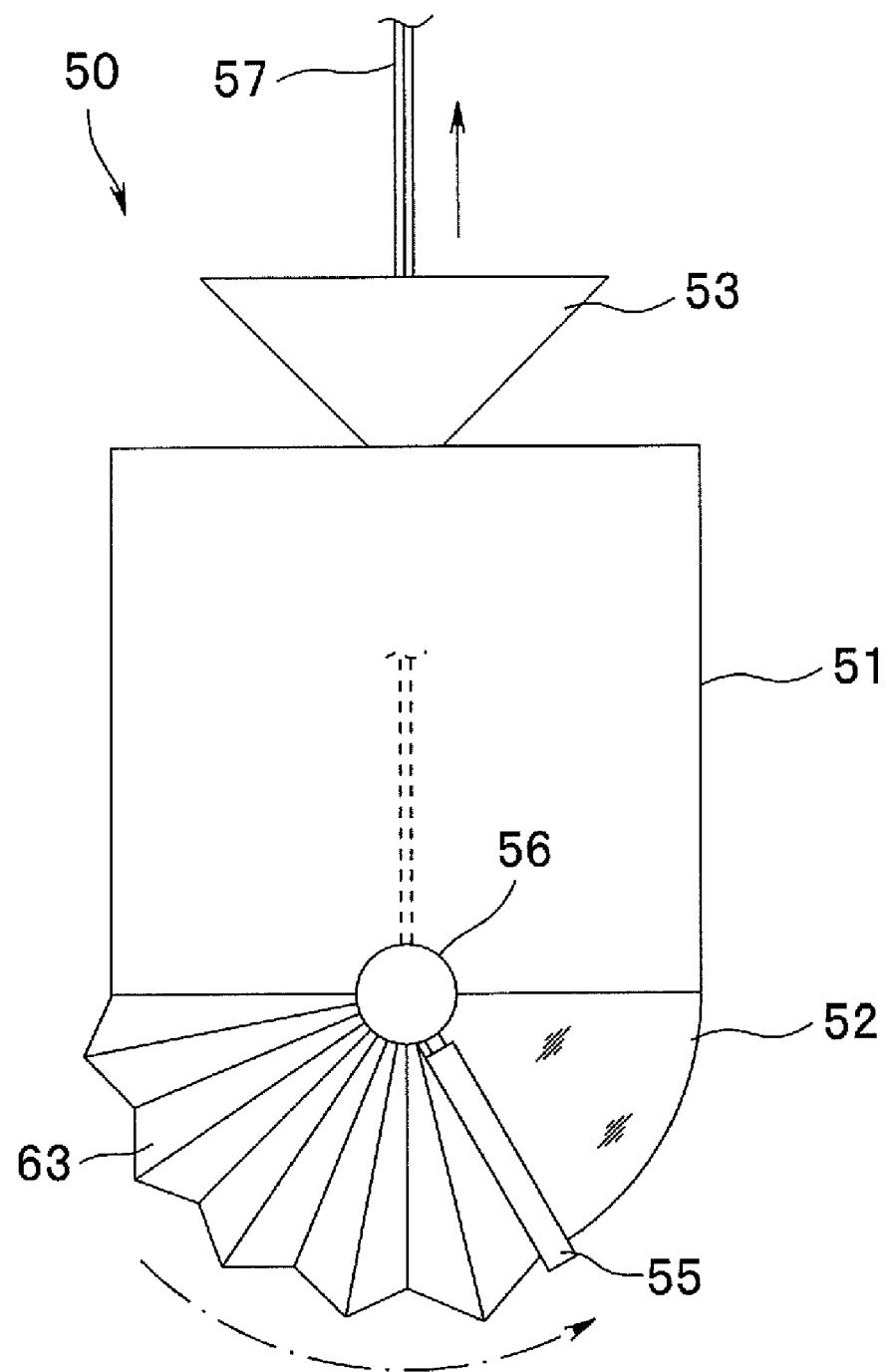
FIG. 23 is a side view illustrating a configuration of a camera set up in the abdominal cavity according to a modification example of the camera set up in the abdominal cavity according to the sixth embodiment of the present invention.

Next, a sixth embodiment of a camera set up in the abdominal cavity, which is a medical instrument of the present invention, will be described below using FIG. 18 to FIG. 23. FIG. 18 to FIG. 23 are related to the sixth embodiment of the present invention, FIG. 18 is a perspective view illustrating a configuration of the camera set up in the abdominal cavity, FIG. 19 is a cross-sectional view illustrating a configuration of a rotation mechanism that rotates a wiper, FIG. 20 is a cross-sectional view along a line XX-XX in FIG. 19, FIG. 21 is an exploded perspective view illustrating a configuration of a rotation mechanism that rotates a wiper according to a modification example, FIG. 22 is a side view illustrating the configuration of the rotation mechanism in FIG. 21 and FIG. 23 is a side view illustrating a configuration of a camera set up in the abdominal cavity according to a modification example.

As shown in FIG. 18, the camera set up in the abdominal cavity (hereinafter simply referred to as "camera") 50 of the present embodiment has a configuration in which a rubber wiper 55 whose cross section is formed into a semi-circular shape rotates and thereby moves while making a sliding contact with the outer surface of a dome-shaped transparent cover 52, which serves as an observation window.

The camera 50 incorporates devices such an image pickup unit, an illumination unit and a transmitter (not shown) in the camera body 51 and is provided with a suction cup 53 similar to those of the above described embodiments, which is an abdominal wall fixing section to be stuck fast and fixed to the body wall (abdominal wall) in the center of the top surface. Two operation wires 57 extend from the center of the suction cup 53.

Furthermore, in the camera body 51, a T-shaped branch pipe 54 is provided which is branched individually and through which the two operation wires 57 pass. The two operation wires 57 are inserted and disposed in the vicinity of the outer circumferential surface of the camera body 51. An end of the operation wire 57 in the camera body 51 is connected to a rotation mechanism 56 to rotate the wiper 55. The rotation mechanism 56 is connected to the wiper 55 via a bar-shaped support body 55a.

The rotation mechanism 56 has a disk-shaped ball support 58 as shown in FIG. 19 and FIG. 20. A concave section 58a having a circular cross section formed in the outer perimeter and a protruding spring support 58b that contacts and holds a compression coil spring 59 are formed in the ball support 58 and a spherical section 55b provided at an end of the support body 55a is disposed in the concave section 58a.

The compression coil spring 59 is disposed inside the concave section 58a of the ball support 58 so as to urge the spherical section 55b of the support body 55a in one direction in the concave section 58a. The operation wire 57 inserted into the hole of the spring support 58b is passed through the compression coil spring 59. The end of the operation wire 57 is connected and fixed to the spherical section 55b.

Thus, in the rotation mechanism 56, when the operation wire 57 is pulled, the spherical section 55b moves along the concave section 58a of the ball support 58 against the urging force of the compression coil spring 59. As the spherical section 55b moves, as shown in FIG. 18, the wiper 55 connected to the support body 55a moves along and in sliding contact with the outer surface of the transparent cover 52.

In the camera 50 configured as described above, when the two operation wires 57 are pulled/slackened, the wiper 55 moves along and in sliding contact with the outer surface of the transparent cover 52 and the wiper 55 can thereby remove deposits stuck to the outer surface of the transparent cover 52.

The rotation mechanism 56 may also be configured to have two hinge members 61 as shown in FIG. 21 and FIG. 22.

To be more specific, in the two hinge members 61, a tabular spring support 61a protrudes from a columnar side peripheral part and a shaft body 62 is inserted into a hole 61b so as to have a configuration in which the two hinge members 61 are connected together in a manner freely rotatable around the shaft body 62.

In the two connected hinge members 61, an end of the compression coil spring 59 is fixed to one side of each spring support 61a, an urging force of the compression coil spring 59 is given in a direction in which the respective spring supports 61a rotate in proximity to each other. One hinge member 61 is fixed to the aforementioned support body 55a (not shown) with an end of the operation wire 57 connected to the spring support 61a. The other hinge member 61 is provided fixed in the rotation mechanism 56.

In the rotation mechanism 56 configured as shown above, when the operation wire 57 is pulled, one hinge member 61 rotates around the shaft body 62 with respect to the other hinge member 61 against the urging force of the compression coil spring 59. The support body 55a connected to the wiper 55 also rotates simultaneously with this.

Therefore, in the camera 50 provided with the above described rotation mechanism 56, when the two operation wires 57 are pulled/slackened, the wiper 55 moves along and in sliding contact with the outer surface of the transparent cover 52, and the wiper 55 can thereby wipe and remove deposits stuck to the outer surface of the transparent cover 52.

Furthermore, as shown in FIG. 23, the camera 50 may also be provided with a bellows-like cover body 63 that covers the dome-shaped transparent cover 52 as the wiper 55 moves. The peripheral edge of the cover body 63 is fixed to the side periphery of the camera body 51 of the camera 50 and the wiper 55 having a semi-circular cross section. When the camera 50 in such a configuration is not used, it is possible to prevent contamination from sticking to the transparent cover 52 by covering the transparent cover 52 with the cover body 63.

Seventh Embodiment

Figure 24:
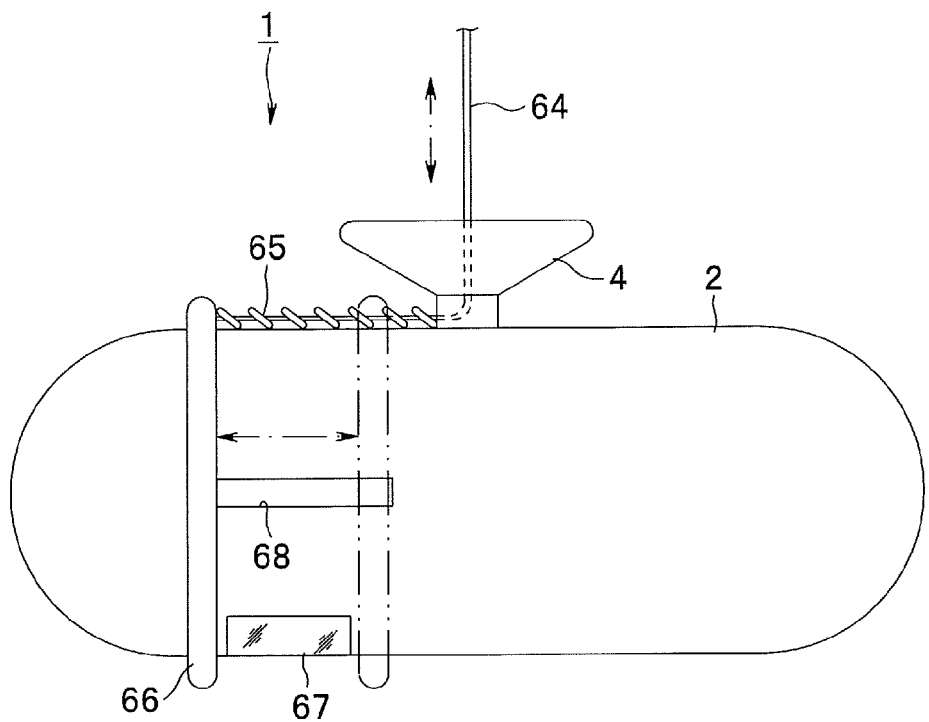
FIG. 24 is a side view illustrating a configuration of a camera set up in the abdominal cavity according to a seventh embodiment of the present invention.
Figure 25:
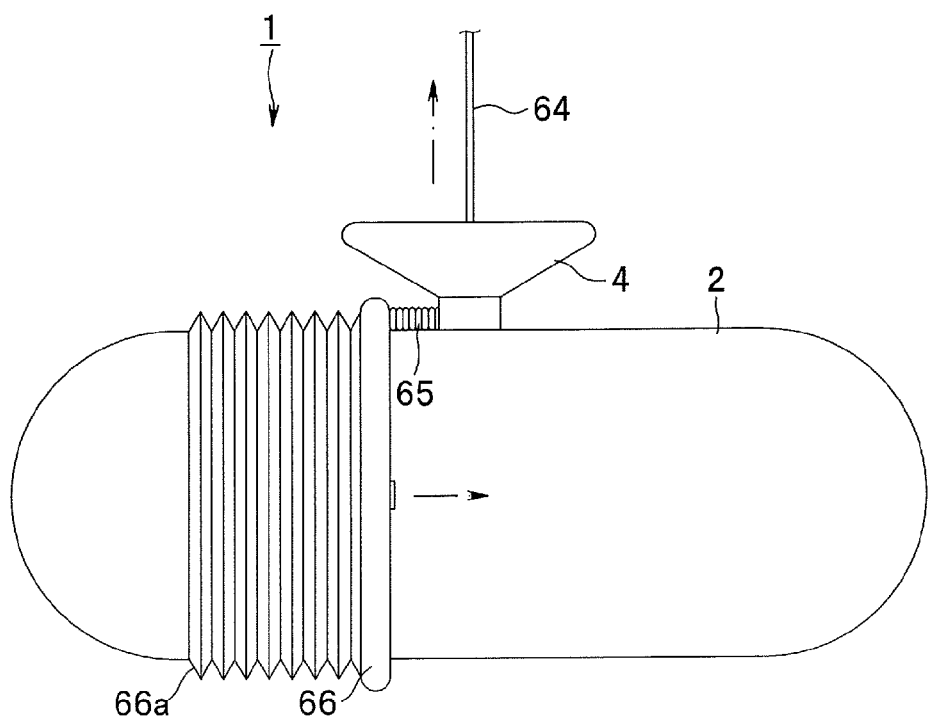
FIG. 25 is a side view illustrating a configuration of a camera set up in the abdominal cavity according to a modification example of the camera set up in the abdominal cavity according to the seventh embodiment of the present invention.

Next, a seventh embodiment of a camera set up in the abdominal cavity, which is a medical instrument of the present invention, will be described below using FIG. 24 and FIG. 25. FIG. 24 and FIG. 25 are related to the seventh embodiment of the present invention, FIG. 24 is a side view illustrating a configuration of the camera set up in the abdominal cavity and FIG. 25 is a side view illustrating a configuration of a camera set up in the abdominal cavity according to a modification example. In the following descriptions, the same components as those in the camera set up in the abdominal cavity of the first embodiment will be assigned the same reference numerals and descriptions of those components and operations and/or effects will be omitted.

As shown in FIG. 24, the camera 1 of the present embodiment has a configuration in which, when an operation wire 64 is manually pulled/slackened, a ring-shaped rubber wiper 66 moves along and in sliding contact with the outer surface of a transparent cover member 67 disposed on an observation window.

The ring-shaped wiper 66 is externally fitted on the outer circumference of the camera body 2 and an end of the operation wire 64 is connected to the top end thereof. One end of the operation wire 64 extends from the suction cup 4 and the other end is led out of the root of the suction cup 4 and disposed along the top surface of the camera body 2.

Furthermore, the operation wire 64 is inserted into the wiper 66 and a compression coil spring 65 whose end contacts the root of the suction cup 4. The compression coil spring 65 urges the wiper 66 in a direction in which the wiper 66 goes away from the suction cup 4.

The wiper 66 is guided in a rectilinear direction by a guide groove 68 formed in the camera body 2.

In the camera 1 of the present embodiment configured as shown above, when the operation wire 64 is pulled, the wiper 66 moves along and in sliding contact with the outer surface of the cover member 67 against the urging force of the compression coil spring 65, and can thereby remove deposits stuck to the outer surface of the cover member 67. Furthermore, when the operation wire 64 is slackened, the wiper 66 slides in the other direction by receiving the urging force of the compression coil spring 65.

As shown in FIG. 25, in the same way as in the seventh embodiment, the camera 1 may also be provided with a cover body 66a which is a bellows-shaped tubular body that expands/contracts as the wiper 66 moves to cover the cover member 67. Thus, when the camera 1 is not used, the cover member 67 is covered with the cover body 66a, and it is thereby possible to prevent contamination from sticking to the cover member 67.

Eighth Embodiment

Figure 26:
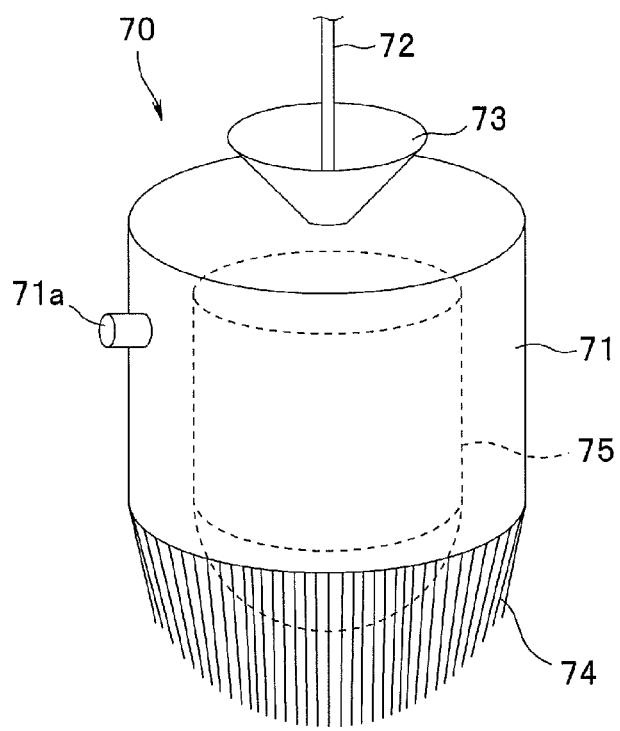
FIG. 26 is a perspective view illustrating a configuration of the camera set up in the abdominal cavity according to an eighth embodiment of the present invention when a camera unit is retracted into a case body.
Figure 27:
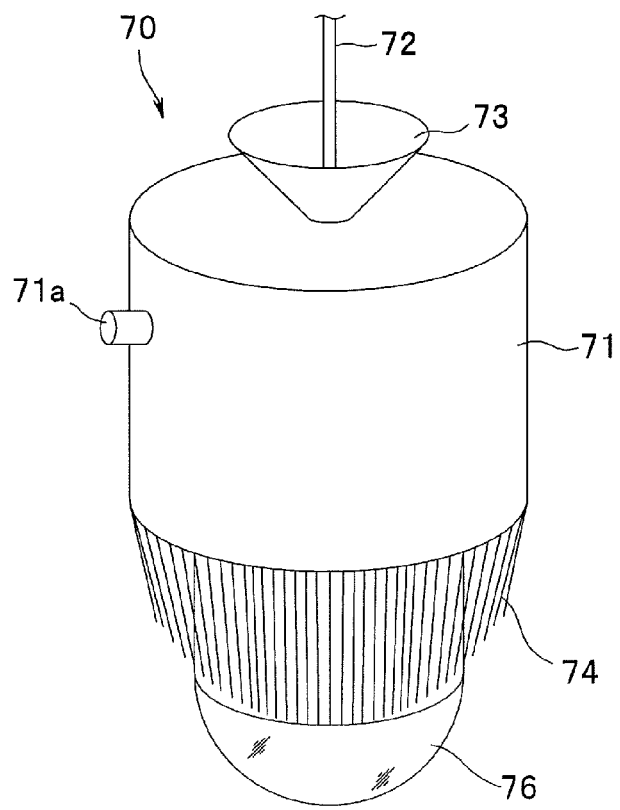
FIG. 27 is a perspective view illustrating a configuration of the camera set up in the abdominal cavity according to the eighth embodiment of the present invention when the camera unit has come out of the case body.
Figure 28:
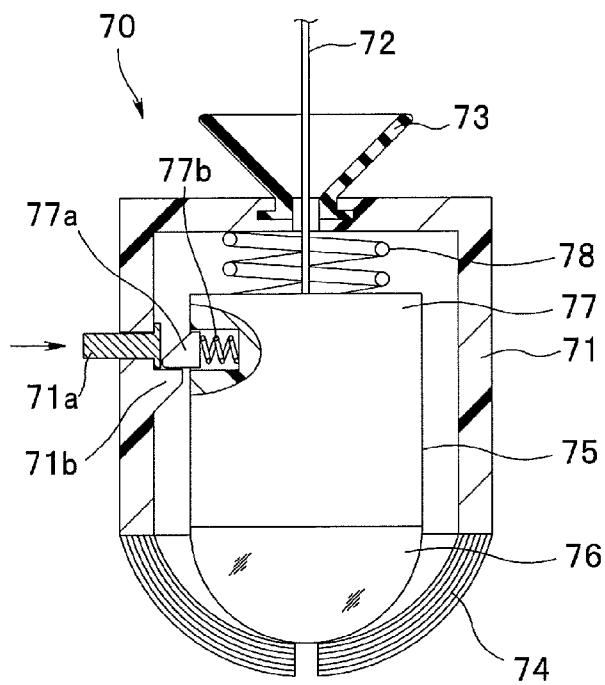
FIG. 28 is a cross-sectional view illustrating a configuration of the camera set up in the abdominal cavity according to the eighth embodiment of the present invention when the camera unit is retracted into the case body.
Figure 29:
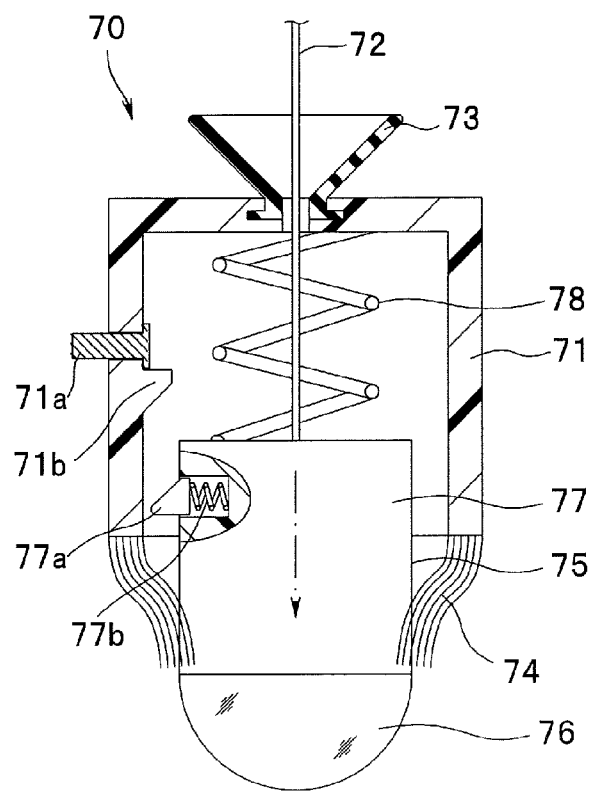
FIG. 29 is a cross-sectional view illustrating a configuration of the camera set up in the abdominal cavity according to the eighth embodiment of the present invention when the camera unit has come out of the case body.

Next, an eighth embodiment of a camera set up in the abdominal cavity, which is a medical instrument of the present invention, will be described below using FIG. 26 to FIG. 29. FIG. 26 to FIG. 29 are related to the eighth embodiment of the present invention, FIG. 26 is a perspective view illustrating a configuration of the camera set up in the abdominal cavity when a camera unit is retracted into a case body, FIG. 27 is a perspective view illustrating a configuration of the camera set up in the abdominal cavity when the camera unit has come out of the case body, FIG. 28 is a cross-sectional view illustrating a configuration of the camera set up in the abdominal cavity when the camera unit is retracted into the case body and FIG. 29 is a cross-sectional view illustrating a configuration of the camera set up in the abdominal cavity when the camera unit has come out of the case body.

The camera set up in the abdominal cavity (hereinafter simply referred to as "camera") 70 of the present embodiment shown in FIG. 26 to FIG. 29 is configured by including a cylindrical case body 71 whose one end is open and a camera unit 75 that protrudes or retracts from the case body 71.

The case body 71 is provided with a suction cup 73, which is an abdominal wall fixing section, from the top surface of which an operation wire 72 extends and has a brush-like rubber wiper 74 fixed around the opening. Furthermore, a compression coil spring 78 is provided in the case body 71, one end of which is fixed to the camera unit 75 and the other end of the compression coil spring 78 is fixed to the inner surface of the top end. Furthermore, a button 71a is provided on the side periphery of the case body 71 and a protrusion 71b is formed in the inside perimeter below the position where the button 71a is provided.

The camera unit 75 has a so-called "capsule endoscope" shape including a dome-shaped transparent cover 76 that constitutes an observation window and a camera body 77 with the transparent cover 76 disposed at an end thereof.

A compression coil spring 78 is fixed at the top end of the camera body 77 and an end of the operation wire 72 is connected to the center of the top end thereof. Furthermore, a protrusion piece 77a is provided on the side of the camera body 77 and the camera body 77 has a compression coil spring 77b that urges the protrusion piece 77a in the outside direction.

The camera unit 75 is accommodated in the case body 71 with the protrusion piece 77a being hooked onto the protrusion 71b of the case body 71 against the urging force of the compression coil spring 78.

Furthermore, when the button 71a of the case body 71 is pushed by a forceps or the like, the protrusion piece 77a of the camera unit 75 retracts into the camera body 77 against the urging force of the compression coil spring 77b and overleaps the protrusion 71b of the case body 71. The transparent cover 76 of the camera unit 75 then juts out of the opening of the case body 71 by the urging force of the compression coil spring 78. The camera unit 75 juts out of the case body 71 up to a balanced position of the compression coil spring 78.

In this case, the transparent cover 76 moves with the outer surface thereof making a sliding contact with the brush-like wiper 74 provided at the opening of the case body 71. Thus, in the camera unit 75 of the camera 70, the brush-like wiper 74 removes contamination or the like stuck to the outer surface of the transparent cover 76. Furthermore, when the operation wire 72 is pulled, the camera unit 75 of the camera 70 retracts into the case body 71 against the urging force of the compression coil spring 78.

By causing the camera unit 75 to jut out or retract from the case body 71, the camera 70 of the present embodiment in such a configuration can remove contamination from the outer surface of the transparent cover 76 using the brush-like wiper 74.

Ninth Embodiment

Figure 30:
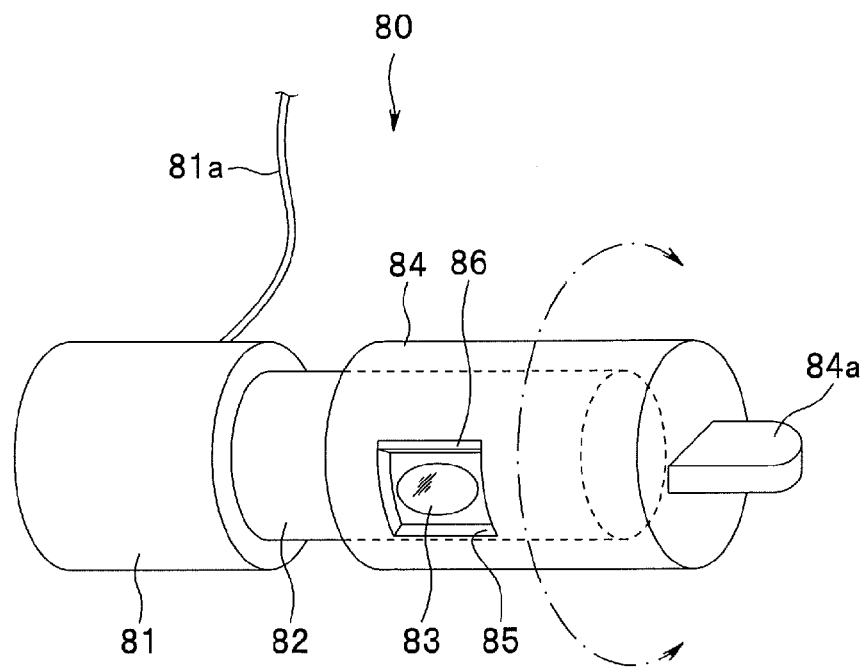
FIG. 30 is a perspective view illustrating a configuration of a camera set up in the abdominal cavity according to a ninth embodiment of the present invention.
Figure 31:
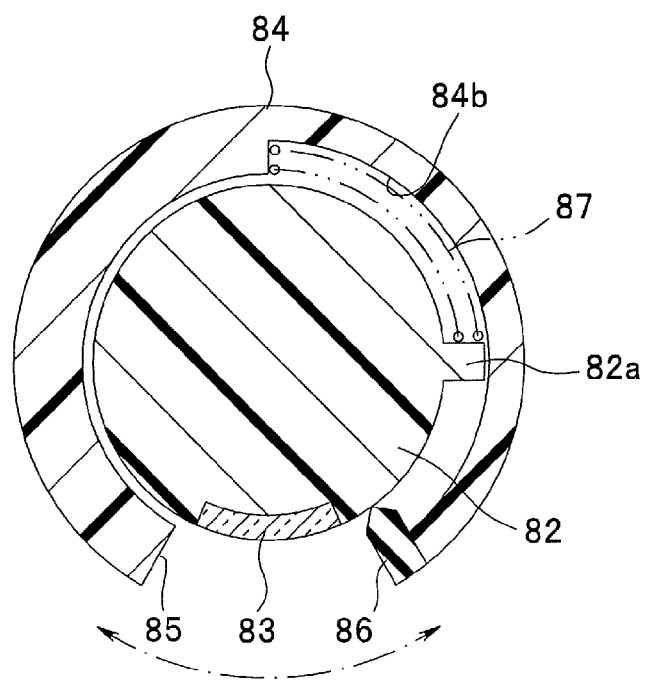
FIG. 31 is a cross-sectional view of the camera set up in the abdominal cavity according to the ninth embodiment of the present invention in FIG. 30.
Figure 32:
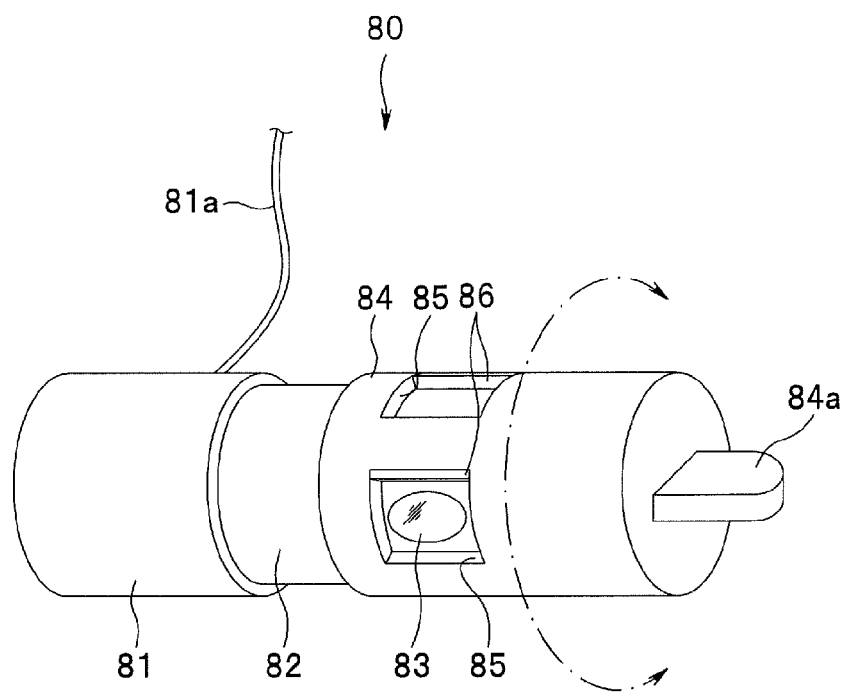
FIG. 32 is a perspective view illustrating a configuration of a camera set up in the abdominal cavity according to a first modification example of the camera set up in the abdominal cavity according to the ninth embodiment of the present invention.
Figure 33:
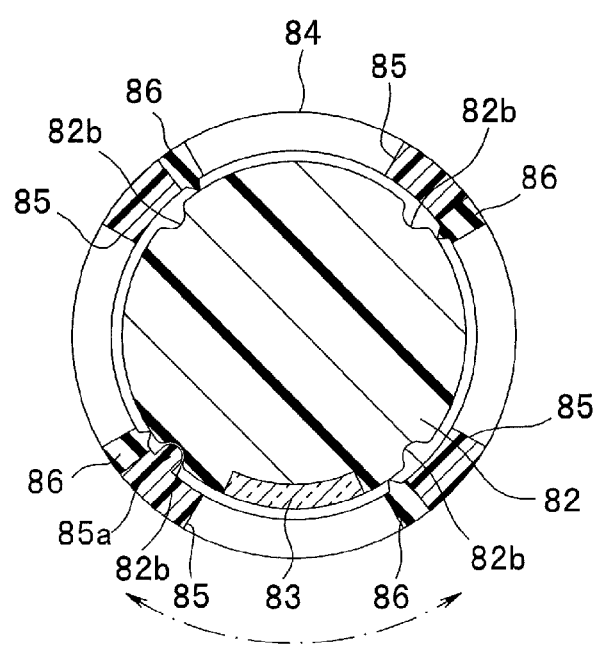
FIG. 33 is a cross-sectional view of the camera set up in the abdominal cavity according to the first modification example of the camera set up in the abdominal cavity according to the ninth embodiment of the present invention in FIG. 32.
Figure 34:
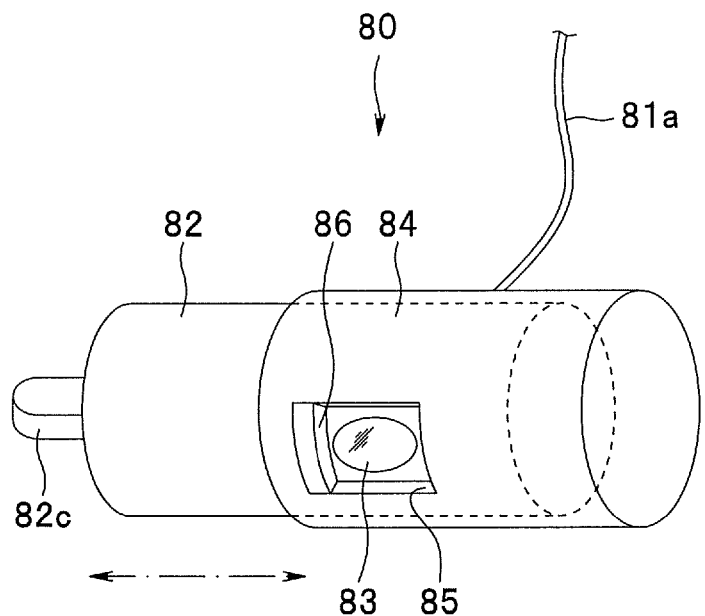
FIG. 34 is a perspective view illustrating a configuration of a camera set up in the abdominal cavity according to a second modification example of the camera set up in the abdominal cavity according to the ninth embodiment of the present invention.
Figure 35:
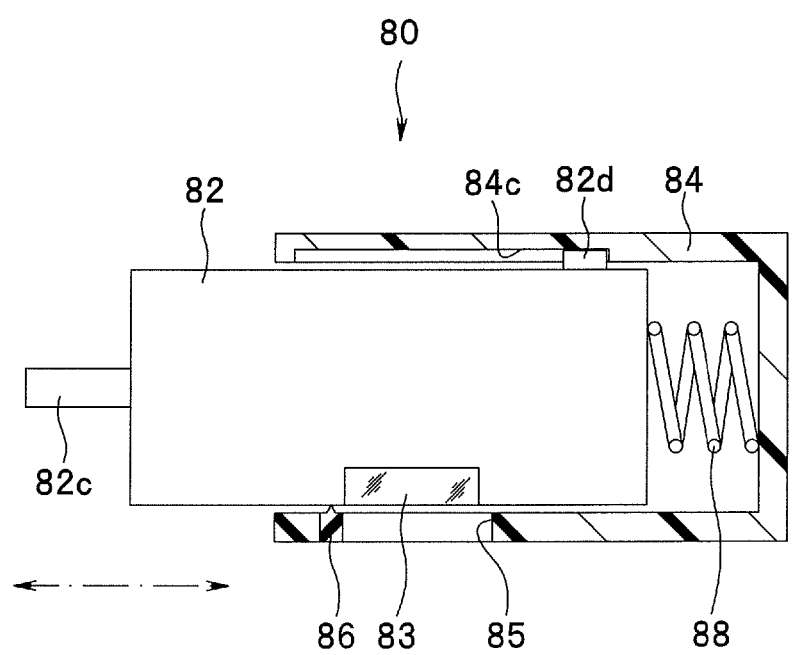
FIG. 35 is a cross-sectional view of the camera set up in the abdominal cavity according to the second modification example of the camera set up in the abdominal cavity according to the ninth embodiment of the present invention in FIG. 34.

Next, a ninth embodiment of a camera set up in the abdominal cavity, which is a medical instrument of the present invention, will be described below using FIG. 30 to FIG. 35. FIG. 30 to FIG. 35 are related to the ninth embodiment of the present invention, FIG. 30 is a perspective view illustrating a configuration of the camera set up in the abdominal cavity, FIG. 31 is a cross-sectional view of the camera set up in the abdominal cavity in FIG. 30, FIG. 32 is a perspective view illustrating a configuration of a camera set up in the abdominal cavity according to a first modification example, FIG. 33 is a cross-sectional view of the camera set up in the abdominal cavity in FIG. 32, FIG. 34 is a perspective view illustrating a configuration of a camera set up in the abdominal cavity according to a second modification example and FIG. 35 is a cross-sectional view of the camera set up in the abdominal cavity in FIG. 34.

As shown in FIG. 30 and FIG. 31, as in the case of the first embodiment, the camera set up in the abdominal cavity (hereinafter simply referred to as "camera") 80 of the present embodiment is configured by including a body section 81 from which a wire 81a extends which is pulled to fix the camera to the abdominal wall 102 in the abdominal cavity 101, a camera unit 82 and a cylindrical cover body 84 that covers the camera unit 82 and is rotatably disposed around the perimeter by means of a bearing (not shown) or the like.

The body section 81 and the camera unit 82 are formed as one piece and have columnar shapes of different diameters. The camera unit 82 is provided with a cover member 83 which constitutes an observation window of a built-in image pickup unit on the perimeter thereof.

An opening 85 is formed in part of the perimeter of the cylindrical cover body 84 and a rubber wiper 86 is provided at one edge of the opening 85. The longitudinal direction orthogonal to the rotation direction of the cylindrical cover body 84 of the wiper 86 is defined and the wiper 86 is provided at one edge of the opening 85 orthogonal to the rotation direction.

The opening 85 is formed at a predetermined rotation position of the cylindrical cover body 84 with respect to the camera unit 82, which is a position at which the cover member 83 of the camera unit 82 is exposed. Furthermore, the cylindrical cover body 84 is provided with a grasping portion 84a which protrudes from one end face so as to be rotated with respect to the camera unit 82 by a forceps or the like.

A compression coil spring 87 is disposed between the camera unit 82 and the cylindrical cover body 84. The compression coil spring 87 is disposed so as to contact a spring support 82a that protrudes from the perimeter of the camera unit 82 and an end face of a groove 84b formed in the inner surface of the cylindrical cover body 84 and urges the cylindrical cover body 84 that rotates with respect to the camera unit 82 in a predetermined direction.

The compression coil spring 87 is set up, accommodated in the groove 84b of the cylindrical cover body 84 so that the cylindrical cover body 84 stops at a position where the cover member 83 of the camera unit 82 is exposed from the opening 85.

In the camera 80 configured as shown above, when the cylindrical cover body 84 is operated to rotate around the perimeter of the camera unit 82, the wiper 86 disposed at the opening 85 makes a sliding contact with the cover member 83 of the camera unit 82. Thus, the camera 80 in such a configuration can also easily remove contamination from the outer surface of the cover member 83 using the wiper 86.

Furthermore, the camera 80 is operated to rotate by grasping the grasping portion 84a of the cylindrical cover body 84 using a forceps or the like to remove contamination from the outer surface of the cover member 83, but when the forceps or the like is detached from the grasping portion 84a to stop the rotation operation, the cylindrical cover body 84 naturally rotates to the position where the cover member 83 of the camera unit 82 is exposed from the opening 85 by the urging force of the compression coil spring 87 and stops.

First Modification Example

As shown in FIG. 32 and FIG. 33, the camera 80 may also include a plurality of openings 85 provided with the wiper 86 arranged in the cylindrical cover body 84.

A plurality of (here four) openings 85 are formed in substantially uniform spacing along the outer circumferential direction of the cylindrical cover body 84 in the camera 80. Furthermore, a protrusion 85a is formed in the inner surface between the neighboring predetermined openings 85 of the cylindrical cover body 84 and when the protrusion 85a is fitted into any one of the four concave sections 82b formed on the perimeter of the camera unit 82, the position where the rotation with respect to the camera unit 82 is stopped is determined.

That is, the protrusion 85a is fitted into any one of the four concave sections 82b formed on the perimeter of the camera unit 82 at a position where the cover member 83 of the camera unit 82 is exposed from any one of the four openings 85. Therefore, the camera 80 is configured such that the cylindrical cover body 84 does not rotate unless a rotation force is given whereby the protrusion 85a can overleap the concave sections 82b.

In the camera 80 in such a configuration, when the cylindrical cover body 84 is operated to rotate around the perimeter of the camera unit 82, any one of the wipers 86 provided at the four openings 85 makes a sliding contact with the cover member 83 of the camera unit 82. This allows the camera 80 to easily remove contamination from the outer surface of the cover member 83 using the wiper 86.

Second Modification Example

As shown in FIG. 34 and FIG. 35, the camera 80 may also be configured such that the camera unit 82 is made to move sliding with respect to the cylindrical cover body 84 so as to remove contamination from the outer surface of the cover member 83 of the camera unit 82 using the wiper 86.

The camera 80 is provided with a grasping portion 82c for grasping using a forceps or the like on one end face of the camera unit 82. Furthermore, a wire 81a which is pulled to fix the camera to the abdominal wall 102 in the abdominal cavity 101 extends from the perimeter of the cylindrical cover body 84.

The longitudinal direction orthogonal to the sliding direction of the camera unit 82 of the wiper 86 here is defined and the wiper 86 is provided at an edge of the opening 85 orthogonal to the sliding direction.

Furthermore, the camera unit 82 is connected to the inner end face of the cylindrical cover body 84 by means of a compression coil spring 88 fixed to the end face inside the cylindrical cover body 84. The urging force of the compression coil spring 88 is set so that the camera unit 82 stops at a position where the cover member 83 of the camera unit 82 is exposed from the opening 85 of the cylindrical cover body 84.

Furthermore, the camera unit 82 is provided with a protrusion 82d on the perimeter in the cylindrical cover body 84. The protrusion 82d is inserted along a guide groove 84c formed in the inner surface of the cylindrical cover body 84 to serve as a rectilinear movement guide in the direction in which the camera unit 82 moves sliding with respect to the cylindrical cover body 84.

In the camera 80 in such a configuration, when the camera unit 82 is operated to slide with respect to the cylindrical cover body 84, the wiper 86 provided at the opening 85 makes a sliding contact with the cover member 83 of the camera unit 82. This allows the camera 80 to easily remove contamination from the outer surface of the cover member 83 using the wiper 86.

According to the medical instruments of the aforementioned embodiments, it is possible to easily and reliably remove deposits stuck to the observation window and obtain a clear observation image even when deposits are being removed.

What is claimed is:

1. A medical instrument including a mechanism for removing contamination on an observation window and used by being introduced into a body and fixed thereto, the medical instrument comprising:

a camera body provided with a fixing section to be fixed to a body wall in the body;

an image pickup section incorporated in the camera body that picks up an image of an object to be examined in the body from an observation window formed in the camera body;

a contamination removing section made of an elastic member and provided by being fixed to the camera body;

a transparent cover member, an outer surface of which is in contact with the contamination removing section, provided on the observation window, disposed on the observation window rotatably around an axis along a longitudinal direction of the camera body, having a cylindrical shape with the axis along the longitudinal direction of the camera body serving as a center axis, and rotated in circumferential direction by the drive section; and a drive section incorporated in the camera body that drives the cover member to make a sliding contact between the contamination removing section and the outer surface of the cover member.

2. The medical instrument including a mechanism for removing contamination on an observation window according to claim 1, wherein the drive section is a motor and moves the cover member to make a sliding contact of the cover member with the contamination removing section.

3. The medical instrument according to claim 1, wherein the drive section is an electromagnet and moves the cover member to make a sliding contact with the contamination removing section.

4. The medical instrument according to claim 1, wherein the cover member has a tabular shape and is made to move sliding by the drive section.

5. The medical instrument including a mechanism for removing contamination on an observation window according to claim 1, wherein:

the camera body has a capsule shape with a cylindrical structure, the longitudinal axis of the cover member is common with the center axis of the camera body, and the drive section rotates the cover member around the center axis of the camera body.

6. The medical instrument including a mechanism for removing contamination on an observation window according to claim 1, wherein the contamination removing section is orthogonal to a rotation direction of the cover member and provided so as to be located outside an image taking region of the camera body.

* * * * *

UNITED STATES PATENT AND TRADEMARK OFFICE
CERTIFICATE OF CORRECTION

PATENT NO. : 8,237,782 B2
APPLICATION NO. : 12/719329
DATED : August 7, 2012
INVENTOR(S) : Hitoshi Karasawa et al.

It is certified that error appears in the above-identified patent and that said Letters Patent is hereby corrected as shown below:

It Should Read:

Column 19, line 20 (claim 3, line 1): The medical instrument including a mechanism for removing contamination on an observation window according to claim 1, wherein Column 20, line 1 (claim 4, line 1): The medical instrument including a mechanism for removing contamination on an observation window according to claim 1, wherein Signed and Sealed this
Ninth Day of April, 2013

Teresa Stanek Rea
*Acting Director of the United States Patent and Trademark Office*